(12) United States Patent
Apt et al.

(10) Patent No.: US 8,735,109 B2
(45) Date of Patent: *May 27, 2014

(54) YEAST STRAINS AND THEIR USES IN THE PRODUCTION OF LIPIDS

(75) Inventors: Kirk E. Apt, Columbia, MD (US); William R. Barclay, Boulder, CO (US); Paul Warren Behrens, Columbia, MD (US)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/634,124

(22) PCT Filed: Mar. 11, 2011

(86) PCT No.: PCT/US2011/028122
§ 371 (c)(1),
(2), (4) Date: Nov. 26, 2012

(87) PCT Pub. No.: WO2011/112948
PCT Pub. Date: Sep. 15, 2011

(65) Prior Publication Data
US 2013/0122557 A1 May 16, 2013

Related U.S. Application Data

(60) Provisional application No. 61/313,055, filed on Mar. 11, 2010, provisional application No. 61/445,469, filed on Feb. 22, 2011.

(51) Int. Cl.
*C12P 7/64* (2006.01)
*C12N 1/00* (2006.01)

(52) U.S. Cl.
USPC ...................................... 435/134; 435/255.1

(58) Field of Classification Search
CPC ...... C12R 1/645; C12P 7/6409; C12P 7/6427
USPC .............................................. 435/134, 255.1
See application file for complete search history.

(56) References Cited

U.S. PATENT DOCUMENTS

| | | | |
|---|---|---|---|
| 4,308,350 A | 12/1981 | Matsuo et al. | |
| 2009/0064567 A1* | 3/2009 | Lippmeier et al. | 44/308 |
| 2012/0034493 A1* | 2/2012 | Apt et al. | 424/93.3 |
| 2012/0323029 A1* | 12/2012 | Pfeifer et al. | 554/224 |
| 2013/0160353 A1* | 6/2013 | Shea et al. | 44/308 |

OTHER PUBLICATIONS

International Search Report for PCT/US2011/028122 mailed Jun. 15, 2011.
Rau et al., "Downstream Processing of Mannosylerythritol Lipids Produced by Pseudozyma Aphidis", Eur J Lipid Sci Technol, 2005, vol. 107, pp. 373-380; abstract, p. 373, fig. 1.
Avis et al., "Specificity and Mode of Action of the Antifungal Fatty Acid cis-9-Heptadecenoic Acid Produced by Pseudozyma Floc-culosa", Applied and Environmental Microbiology, 2001, vo. 67, No. 2, pp. 956-960; p. 956, right col., para 3; p. 958, left col., para 3.
Perrier et al., "Fatty Acid and Carotenoid Composition of Rhodotorula Strains", Arch Microbiol, 1995, vol. 164, No. 3, pp. 173-179; abstract only.
Pathan et al., Diversity of Yeasts from Puddles in the Vicinity of Midre Lovenbreen Glacier, Artic and Bioprospecting for Enzymes and Fatty Acids, Curr Microbiol, Published online: Dec. 5, 2009; p. 308, right col, para 2; p. 309, left col, para 1, Table 1; p. 309, left col, para 1, fig 1; p. 312, Table 3.
Blin-Perrin et al., Metabolism of Ricinoleic Acid into Gamma-Decalactone; Beta-Oxidation and Long Chain Acyl Intermediates of Ricinoleic Acid in the Genus *Sporidiobolus* sp., FEMS Microbiology Letters, 2000, vol. 188, pp. 69-74; p. 72, fig 2D.
Apt et al, U.S. Appl. No. 13/046,065, filed Mar. 11, 2011.
Biomass Energy center at www.direct.gov.uk, Retrieved by Wikipedia Feb. 28, 2012.
Peltroche-Llacsahuanga et al, 2002, "First Isolation of Reddish-Pigmented *Candida* (Torulopsis) *glabrata* from a Clinical Specimen", Journal of Clinical Microbiology, vol. 40, No. 3, pp. 1116-1118.
Joshi et al, 2003, "Microbial Pigments", Indian Journal of Biotechnology, vol. 2, Jul. 2003, pp. 362-369.
Alvarez et al, "Lipid accumulation in *Rhodotorula glutinis* on sugar cane molasses in single-stage continuous culture", World J. Microbiol. Biotechnol. 8:214-215, Rapid Communications of Oxford Ltd. (1992).
Athenstaedt et al, "Lipid particle composition of the yeast *Yarrowia lipolytica* depends on the carbon source", Proteomics 6:1450-1459 (2006).
Dai et al, "Biodiesel generation from oleaginous yeast *Rhodotorula glutinis* with xylose assimilating capacity", African Journal of Biotechnology, vol. 6(18), pp. 2130-2134 (2007).
Davoli et al, "Carotenoids and Fatty Acids in Red Yeasts *Sporobolomyces roseus* and *Rhodotorula glutinis*", Applied Biochemistry and Microbiology, vol. 40, No. 4, pp. 392-397 (2004).
Hammond et al, "Oil Production by candida curvata and Extraction, Composition, and Properties of the Oil, Chapter 14", in New Sources of Fats and Oils, pp. 171-187, Pryde et al., ed., American Oil Chemists' Socieity, United States (1981).
Hassan et al, "Production of Cocoa Butter Equivalents from Prickly-Pear Juice Fermetnation by an Unsaturated Fatty Acid Auxotroph of *Cryptococcus curvatus* Grown in Batch Culture", Process Biochemistry, vol. 30, No. 7, pp. 629-634, 1995.
Johnson et al, "Effect of pH on lipid accumulation by an oleaginous yeast: *Rhodotorula glutinis* IIP-30", World Journal of Microbiology and Biotechnology, 8, 382-384 (1992).
Kessell, "Fatty Acids of *Rhodotorula gracilis*: Fat Production in Submerged Culture and the Particular Effect of pH Value", J. Appl. Bact. 31, 220-231 (1968).
Leman, "Oleaginous Microorganisms: An Assessment of the Potential", Adv. Appl. Microbiol. 43:195-243 (1997).
Misra et al, "Production and Composition of Microbial Fat from *Rhodotorula glutinis*", J. Sci, Food Agric. 35:59-65 (1984).

(Continued)

*Primary Examiner* — Karen Cochrane Carlson
*Assistant Examiner* — Jennifer M. H. Tichy
(74) *Attorney, Agent, or Firm* — Nixon & Vanderhye P.C.

(57) ABSTRACT

The invention is directed to isolated microorganisms, as well as biomasses, cultures, microbial oils, and compositions thereof. The invention also provides methods of producing the microbial oils and methods of using the isolated microorganisms, biomasses, and microbial oils.

45 Claims, 9 Drawing Sheets

(56) References Cited

OTHER PUBLICATIONS

Morita et al, "Discovery of Pseudozyma rugulosa NBRC 10877 as a novel producer of the glycolipid biosurfactants, mannosylerythritol lipids, based on rDNA sequence", Appl. Microbiol. Biotechnol. 73:305-313 (2006).

Moss et al, "Determination of Cellular Fatty Acid Compositions of Various Yeasts by Gas-Liquid Chromatography", Journal of Clinical Microbiology, vol. 16, No. 6, pp. 1073-1079, Dec. 1982.

Papanikolaou et al, "Accumulation of a Cocoa-Butter-Like Lipid by *Yarrowia lipolytica* Cultivated on Agro-Industrial Residues", Current Microbiology, vol. 46, pp. 124-130 (2003).

Rolph et al, Acyl Lipid Metabolism in the Oleaginous Yeast *Rhodotorula gracilis* (CBS 3043), Lipids 24:715-720 (1989).

Ratledge et al, "The Biochemistry and Molecular Biology of Lipid Accumulation in Oleaginous Microorganisms", Advances in Applied Microbiology, vol. 51:1-52 (2002).

Rattray et al, "Chapter 9: Yeasts," in Microbial Lipids, vol. 1, pp. 555-697 (1988).

Saxena et al, "Lipid and Fatty Acid Biosynthesis by *Rhodotorula minuta*", JAOCS, vol. 75, No. 4, pp. 501-505 (1998).

Smit et al, "Production of Cocoa Butter Equivalents by Yeast Mutants", in Industrial Applications of Single Cell Oils, Kyle and Ratledge, eds, American Oil Chemists' Society (1992).

Turcotte et al, "Lipid Biosynthesis in Oleaginous Yeasts", in Advances in Biochemical Engineering 40:73-92 (1989).

Usatai, "Biotechnological Potential of Sporobolomyces Pararoseus CNM-YS-01", Roum. Biotechnol. Lett. vol. 4, No. 1, pp. 83-87 (1999).

Verwoert et al, "Modification of the fatty-acid composition in lipids of the oleaginous yeast *Apiotrichum curvatum* by intraspecific spheroplast fusion", Appl Microbiol Biotechnol, 32:327-333 (1989).

Yamauchi et al, "Mass Production of Lipids by Lipomyces starkeyi in Microcomputer-Aided Fed-Batch Culture", J. Ferment. Technol., vol. 61, No. 3, pp. 275-280 (1983).

Usatii et al, "Yeast Strain Sporobolomyces Pararoseus as Lipides Source", English translation of Application No. MD1997000970112 F1, Republic of Moldova, published Dec. 31, 1997, filed Apr. 22, 1997, 3 pages.

Zaitseva et al, "Change in Chemical Composition of Triacrylglycerols of *Rhodotorula gracilis* as a Function of Specific Growth Rate", in Moscow Technological Institute of the Food Industry, translated from Khimiya Prirodnykh Soedinenii, No. 2, pp. 175-179, Plenum Publishing Corporation, Russia (1988).

* cited by examiner

Figure 1. MK 28428 DNA Sequences

28428 D1D2 sequence

GCATATCAATAAGCGGAGGAAAAGAAACTAACAAGGATTCCCCTAGTAACG
GCGAGTGAAGAGGGAAGAGCCCAAGATTGAAAGCTGGCGTCTTCGGCGTCC
GCATTGTAATCTCAAGAAGTGTTTTCCGCTTCGGACCAAGCCTAAGTCCCTTG
GAAAAGGGCATCATAGAGGGTGATAATCCCGTACATGGCTTGGAGCGCCCGA
AGCTTTGTGATACGCTTTCTAAGAGTCGAGTTGTTTGGGAATGCAGCTCAAAA
TGGGTGGTAAATGCCATCTAAGGCTAAATATTGGGGAGAGACCGATAGCGAA
CAAGTACAGTGATGGAAAGATGAAAAGAACTTTGAAAAGAGAGTTAAACAG
TACGTGAAATTGCCAAAAGGGAAGGGTAGGAGGTCAGAGATGCGGCCTGGG
ATTCAGCCTTGCTTTTGCTTGGTGTTTTTCCCAGATTGCAGGCCAACGTCGGTT
TTGGGCACTGGAGAAGGGTAGGAGGAACGTGGCACCTCTCGGGGTGTGTTAT
AGCCTCCTACTGGATACAGCGACCGAGACCGAGGACAGCAGCGTACTCGCAA
GAGCGGGCCTTCGGGCACCTTTACG

28428 ITS sequence

GTTGATACCATAGGATTTGAACGTAGATGAAACTCGACTGGTAATGCGGTCG
TCTAAAATCTAAAAACAACTTTTGGCAACGGATCTCTTGGTTCTCCCATCGAT
GAAGAACGCAGCGAATTGCGATAAGTAATGTGAATTGCAGAAGTGAATCATC
GAATCTTTGAACGCACCTTGCGCTCCCGGCAGATCTAATCTGGGGAGCATGC
CTGTTTGAGGGCCGCGAATTGTTTCGAACGACAGCTTTCTTATTTAGTTGAGA
AGCTGGCGGATCGGTATTGAGGGTCTTGCCATCTTCCACGGTGGCTCCCTCG
AAATGCATTAGCGCATCCATTCGATAGGCAAGACGGACGAAAGCTCGTTATT
TCGCCCACGTCTTTCCCTGCCGGGTTTTGATAATATCAGGACTTCGGAGAGGA
GAGGCGCAGGGTCGAGGAGCTGGACGCGACGTTTTGCTGGTTGGAGTGCTTC
TGAACCCCGCCCATGCCTCCCTTCTTCGGAAGGAGAGGAAGGGATTTAATTTC
AATTCATCGGCCTCAGATTG

Figure 2. Phylogenetic Tree of MK 28428 D1/D2 DNA sequences.
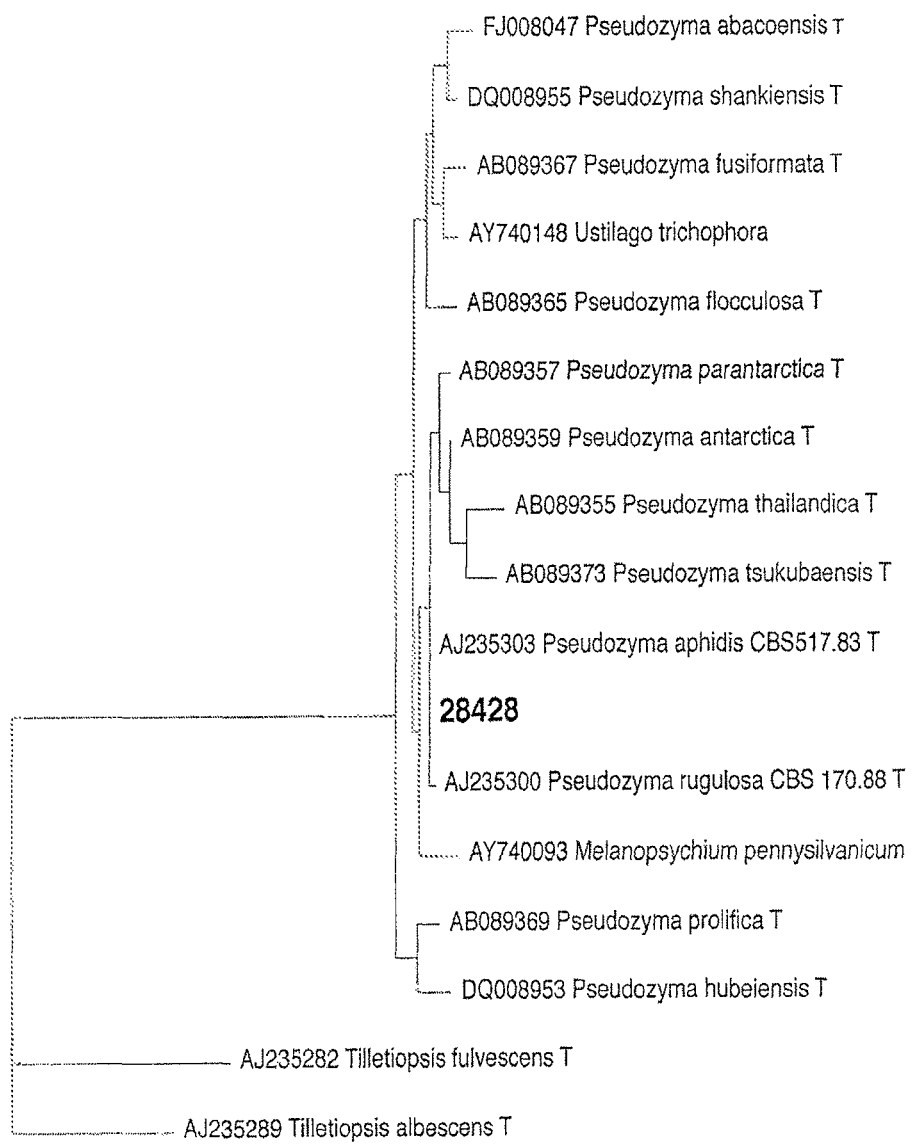

Figure 3. Phylogenetic Tree of MK 28428 ITS DNA sequences
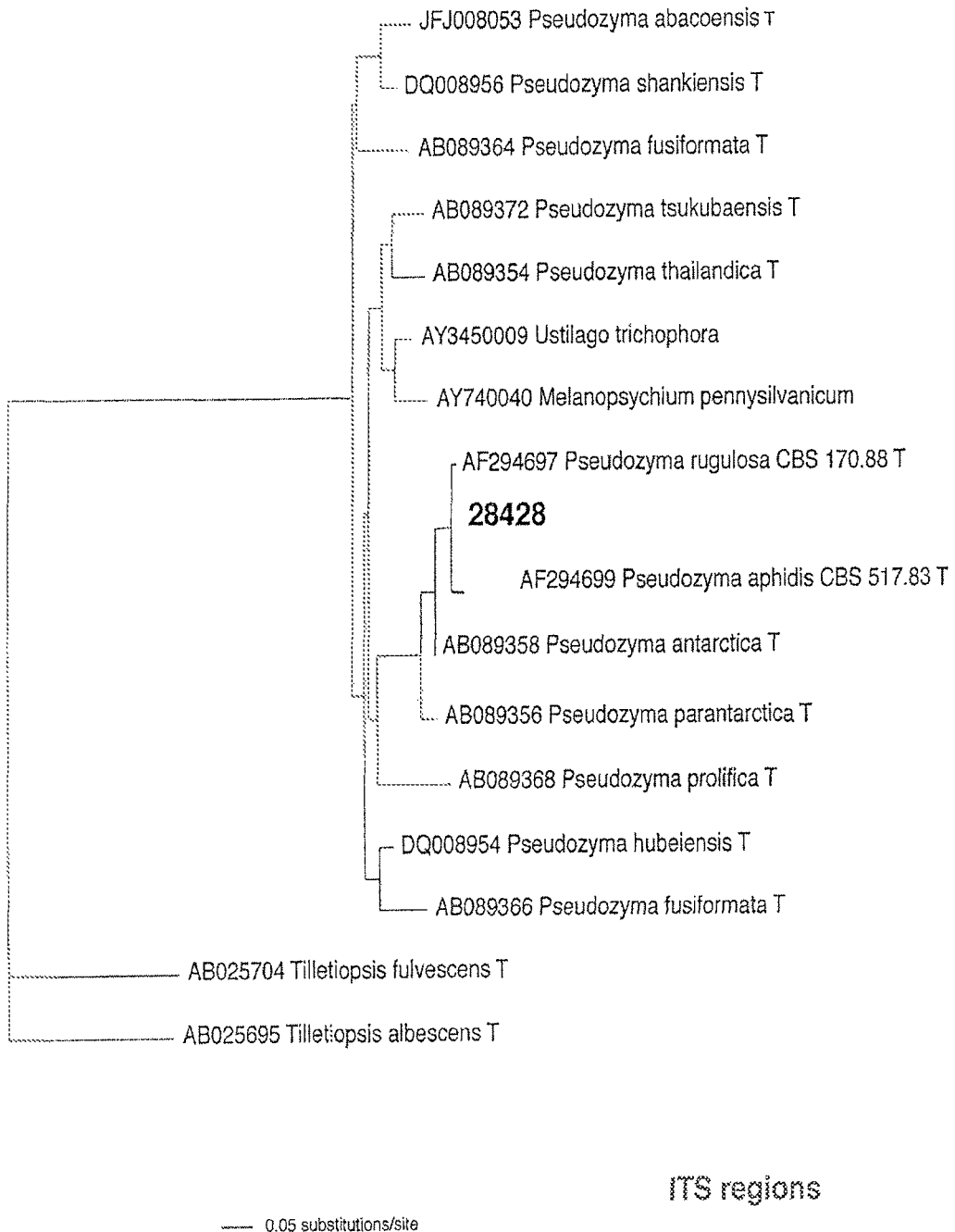

Figure 4. MK 29404 DNA Sequences

29404 D1D2 sequence

ATTCCCCTAGTAGCGGCGAGCGAAGCGGGAAAAGCTCAAATTTGTAATCTGG
CGTCTTCGACGTCCGAGTTGTAATCTCGAGAAGTGTTTTCCGTGATAGACCGC
ATACAAGTCTCTTGGAACAGAGCGTCATAGTGGTGAGAACCCAGTACACGAT
GCGGATGCCTATTACTTTGTGATACACTTTCGAAGAGTCGAGTTGTTTGGGAA
TGCAGCTCAAATTGGGTGGTAAATTCCATCTAAAGCTAAATATTGGCGAGAG
ACCGATAGCGAACAAGTACCGTGAGGGAAAGATGAAAAGCACTTTGGAAAG
AGAGTTAACAGTACGTGAAATTGTTGGAAGGGAAACACATGCAGTGATACTT
GCTATTCGGGGCAACTCGATTGGCAGGCCCGCATCAGTTTTCGGGGCGGAA
AATCGTAGAGAGAAGGTAGCAGTTTCGGCTGTGTTATAGCTCTTTACTGGATT
CGCCCTGGGGGACTGAGGAACGCAGCGTGCTTTTAGCATGAGCTTCGGCTTA
TCCACGCTTAGGATGCGGGTTTATGGCTGTATATGACCCGT 29404 its sequence AACAAGGTTTCCGTAGGTGAACCTGCGGAAGGATCATTATTGAAAACAAGGG
TGTCCAATTTAACTTGGAACCCAAACTTCTCAATTCTAACTTTGTGCATCTGT
ATTAATGGCGAGCAACTTCGGTTGTGAGCCTTCACTTACAAAACACTAGTCTA
TGAATGTAAAATTTTTATAACAAATAAAAACTTTCAACAACGGATCTCTTGGC
TCTCGCATCGATGAAGAACGCAGCGAAATGCGATACGTAATGTGAATTGCAG
AATTCAGTGAATCATCGAATCTTTGAACGCATCTTGCGCTCTCTGGTATTCCG
GAGAGCATGTCTGTTTGAGTGTCATGAATTCTTCAACCCAATCTTTTCTTGTA
ATCGATTGGTGTTTGGATTCTGAGCGTTGCTGGCGTTTGCCTAGCTCGTTCGT
AATACATTAGCATCCCTAATACAAGTTTGGATTGACTTGGCGTAATAGACTAT
TCGCTAAGGATTCGGTGGAAACATCGAGCCAACTTCATTAAGGAAGCTCCTA
ATTTAAAAGTCTACCTTTTGATTAGATCTCA Figure 5. Phylogenetic Tree of MK 29404 D1/D2 DNA sequences.
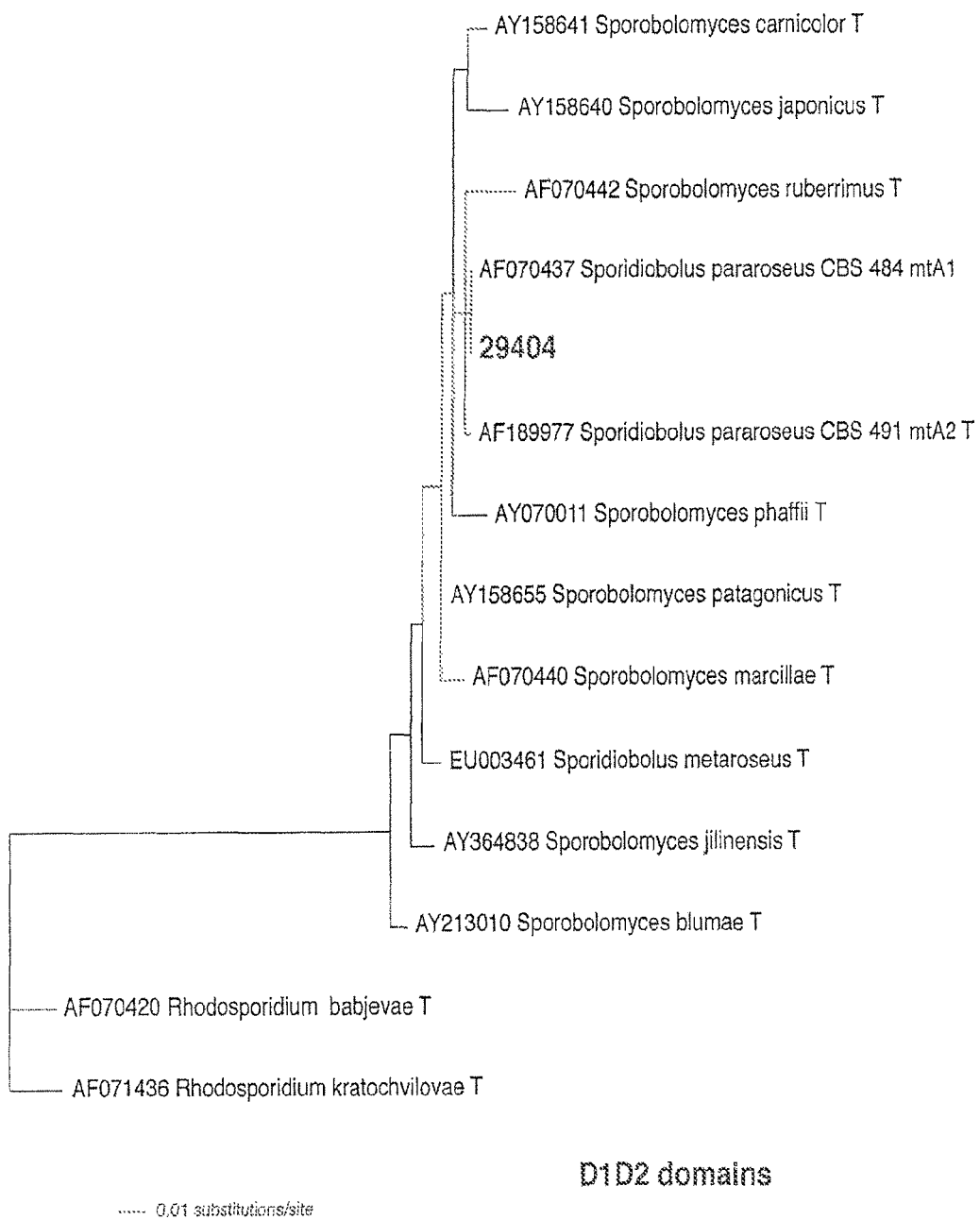

Figure 6. Phylogenetic Tree of MK 29404 ITS DNA sequences
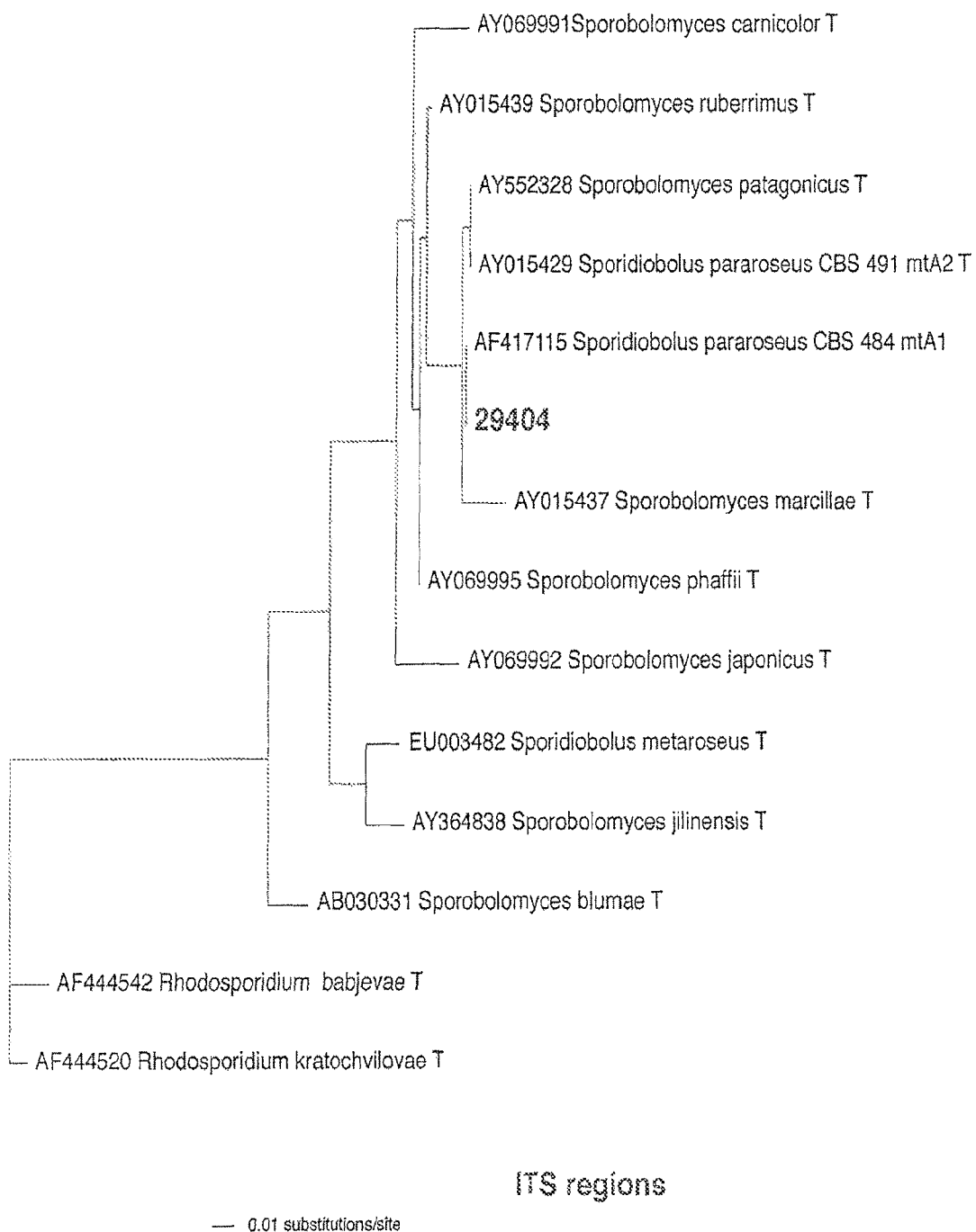

Figure 7. MK 29794 DNA Sequences

29794 D1D2

TAAGCGGAGGAAAAGAAACTAACAAGGATTCCCCTAGTAACGGCGAGTGAA
GCGGGAAGAGCTCAAATTTGTAATCTGGCACTTTCAGTGTCCGAGTTGTAATC
TCGAGAAGTGTTTTCCGCGCCGGACCGCATACAAGTCTGTTGGAATACAGCG
TCATAGTGGTGAGAACCCCGTAACTGATGCGGATGCCCGGTGCTTTGTGATA
CACTTTCGAAGAGTCGAGTTGTTTGGGAATGCAGCTCAAATTGGGTGGTAAA
TTCCATCTAAAGCTAAATATTGGCGAGAGACCGATAGCGAACAAGTACCGTG
AGGGAAAGATGAAAAGCACTTTGGAAAGAGAGTTAACAGTACGTGAAATTG
TTGGAAGGGAAACGCTTGAAGTCAGACTTGCTATTTGGAGTTCAGCCCATGG
TGTATTCTTCAATTTGCAGGCCAGCATCAGTTTTCGAGGGTGGAAAATCGTAG
TTTGAATGTAGCAGTTTCGGCTGTGTTATAGCTTTCTACTGGATTCATCTTTGG
GGACTGAGGAACGCAGTGCGCTTTTAGCAAGGCTCTCGAGCTTTACGCACTT
AGGATGC

29794 ITS

GACCTGCGGAAGGATCATTAGTGAATTTAGCGCATCTGCTTTGCAGAGCGTG
ACCTCCACTTTCTAACTCTGTGCACTTAATGGCGGAAGAGATGAAATATGCTC
TTCTGCGGCTCATTTTATAACACTAGTTAAAGAATGTAACGAAATATCGAAAC
AAAAAAAAACTTTCAACAACGGATCTCTTGGCTCTCGCATCGATGAAGAACG
CAGCGAAATGTGATAAGTAATGTGAATTGCAGAATTCAGTGAATCATCGAAT
CTTTGAACGCACCTTGCGCTCCCTGGTATTCCGGGGAGCATGTCTGTTTGAGT
GTCATGAACTCTTCAACCCACCGGTTTCTTGTAAACTGGCTGGTGTTTGGTTT
CTGAGTGTTGCTCGTTCTTGTGACTGAGCTCATTCGTAATATATGAGCATCTC
TAATTCGAATTCGGATTGACTCAGTGTAATAGACTATTCGCTGAGGACACACC
TAGTGTGGCCGAATAAGATAATTGTAGAAGCTTCTAACCCTTCTAGTCATTTT
AAGATTAGACCTCAGATCAGATAGGACTACCCGCTGAACTTAAGCATATCAA
TAAGCGGAGGA

Figure 8. Phylogenetic Tree of MK 29794 D1/D2 DNA sequences.
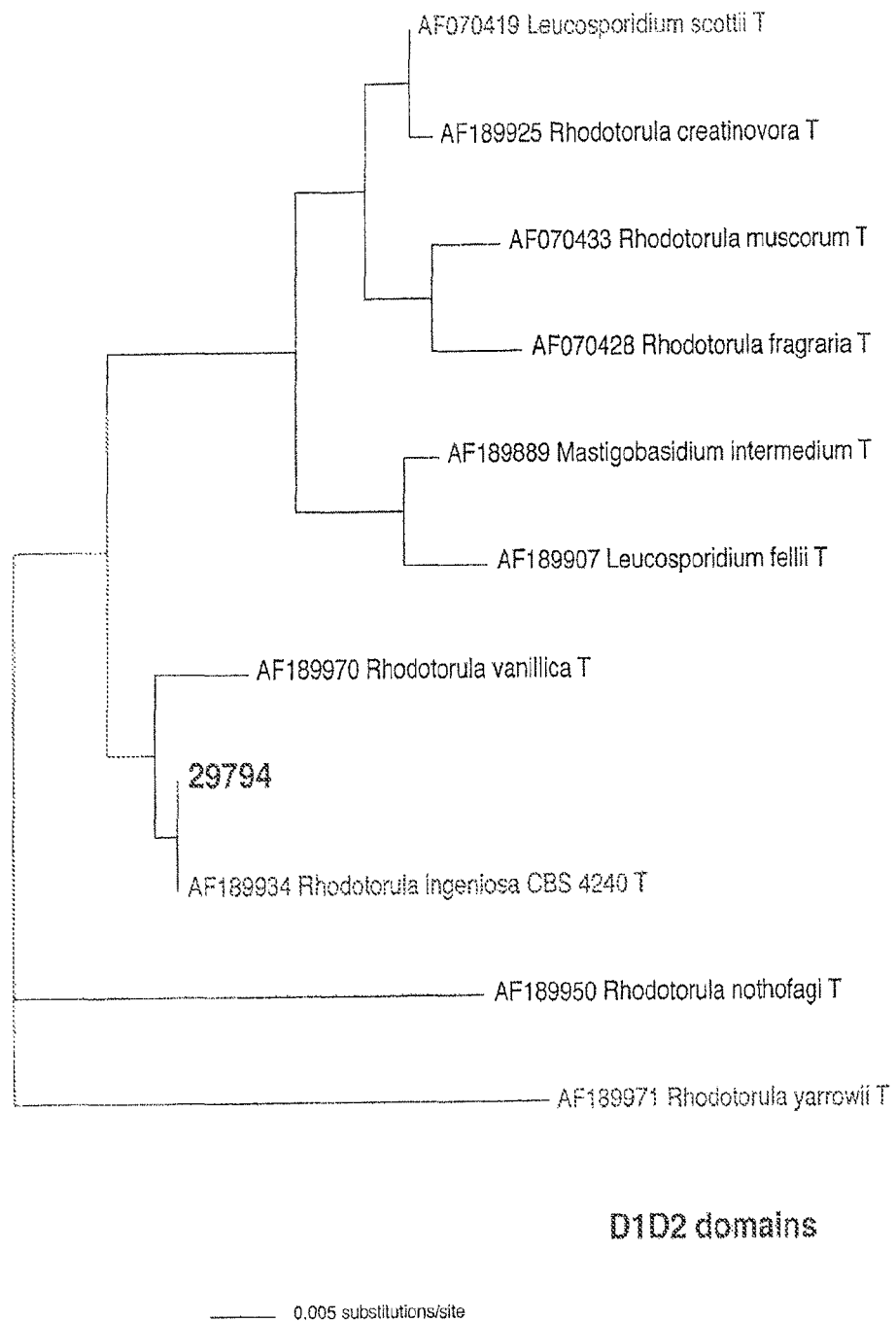

Figure 9. Phylogenetic Tree of MK 29794 ITS DNA sequences
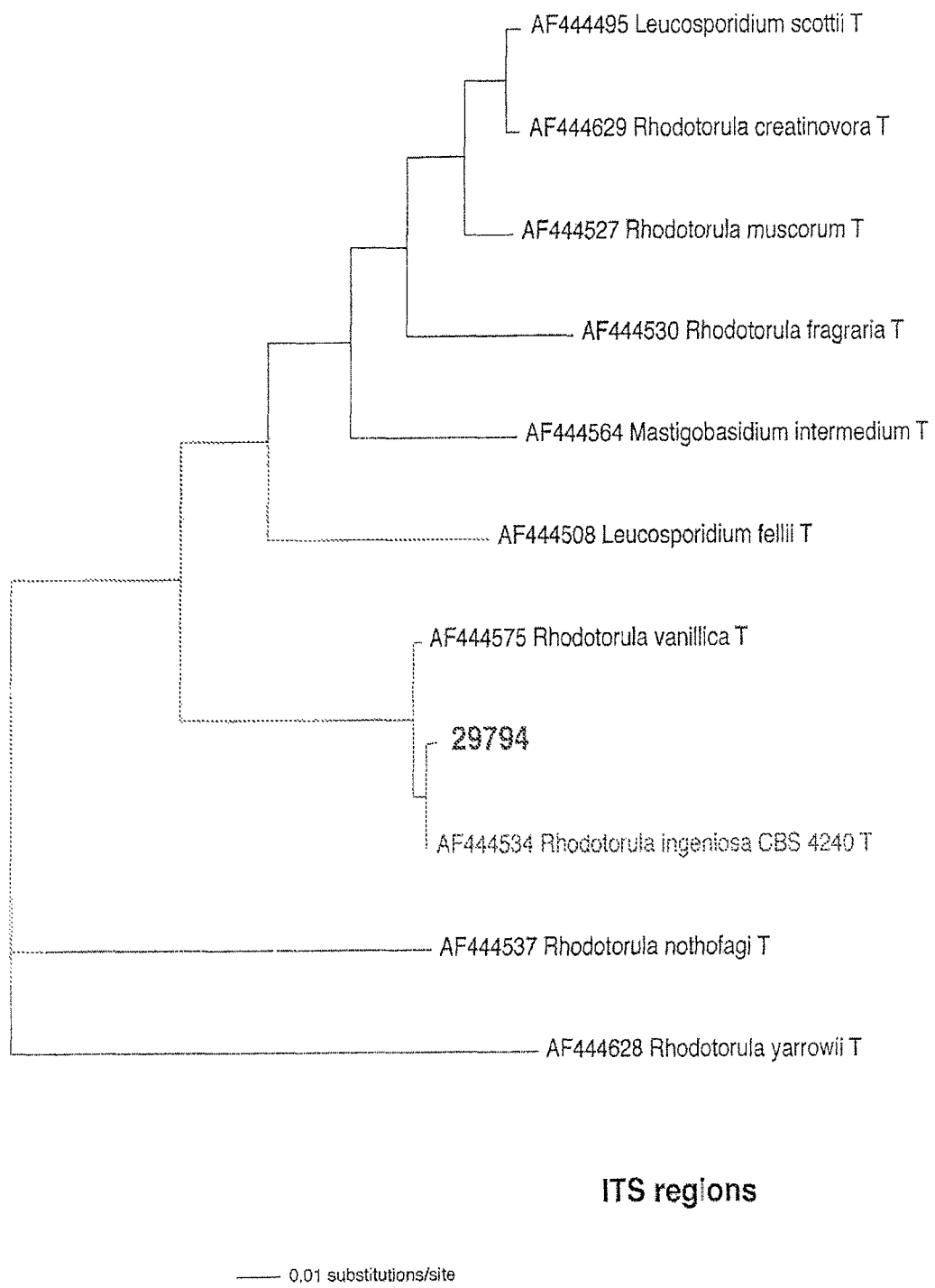

YEAST STRAINS AND THEIR USES IN THE PRODUCTION OF LIPIDS

This application is the U.S. national phase of International Application No. PCT/US2011/028122 filed 11 Mar. 2011 which designated the U.S. and claims priority to U.S. Provisional Application No. 61/313,055 filed 11 Mar. 2010, and U.S. Provisional Application No. 61/445,469 filed 22 Feb. 2011 the entire contents of each of which are hereby incorporated by reference.

BACKGROUND OF THE INVENTION

1. Field of the Invention

The invention is directed to isolated microorganisms, as well as biomasses, cultures, microbial oils, and compositions thereof. The invention also provides methods of producing the microbial oils and methods of using the isolated microorganisms, biomasses, cultures, and microbial oils.

2. Background Art

Fatty acids are classified based on the length and saturation characteristics of the carbon chain. Fatty acids are termed saturated fatty acids when no double bonds are present between the carbon atoms and are termed unsaturated fatty acids when double bonds are present. Unsaturated long chain fatty acids are monounsaturated when only one double bond is present and are polyunsaturated when more than one double bond is present.

Polyunsaturated fatty acids ("PUFAs") are classified based on the position of the first double bond from the methyl end of the fatty acid: omega-3 (n-3) fatty acids contain a first double bond at the third carbon, while omega-6(n-6) fatty acids contain a first double bond at the sixth carbon. For example, docosahexaenoic acid ("DHA") is an omega-3 long chain polyunsaturated fatty acid ("LC-PUFA") with a chain length of 22 carbons and 6 double bonds, often designated as "22:6 n-3." Other omega-3 LC-PUFAs include eicosapentaenoic acid ("EPA"), designated as "20:5 n-3," and omega-3 docosapentaenoic acid ("DPA n-3"), designated as "22:5 n-3." DHA and EPA have been termed "essential" fatty acids. Omega-6 LC-PUFAs include arachidonic acid ("ARA"), designated as "20:4 n-6," and omega-6 docosapentaenoic acid ("DPA n-6"), designated as "22:5 n-6."

The production of biological oils from sources such as plants (including oilseeds), microorganisms, and animals is essential for various purposes. For example, it is desirable to increase the dietary intake of many beneficial nutrients found in biological oils. Particularly beneficial nutrients include fatty acids such as omega-3 and omega-6 fatty acids and esters thereof. Omega-3 fatty acids are recognized as important dietary compounds for preventing arteriosclerosis and coronary heart disease, for alleviating inflammatory conditions and for retarding the growth of tumor cells. Omega-6 fatty acids serve not only as structural lipids in the human body, but also as precursors for a number of factors in inflammation, such as prostaglandins, leukotrienes, and oxylipins.

Because humans and many other animals cannot directly synthesize omega-3 and omega-6 essential fatty acids, they must be obtained in the diet. Traditional dietary sources of essential fatty acids include vegetable oils, marine animal oils, fish oils and oilseeds. In addition, oils produced by certain microorganisms have been found to be rich in essential fatty acids.

Oleic acid is another important beneficial fatty acid. Oleic acid is an omega-9 fatty acid that has been associated with health benefits such as slowing the development of heart disease and promoting the production of antioxidants. It is also used as an ingredient in Lorenzo's oil, a medication developed to prevent the onset of adrenoleukodystrophy (ALD). Oleic acid has also been used as a cosmetic ingredient due to its moisturizing effect.

Linoleic acid is also an example of an important fatty acid. It is an unsaturated omega-6 fatty acid that is essential to various biological processes, such as those involved in hair loss, wound healing, cystic fibrosis, dermatitis, and diabetes. Linoleic acid is also used as a cosmetic ingredient due to its beneficial effects on the skin, and in the making of soaps and emulsifiers.

In order to reduce the costs associated with the production of beneficial fatty acids for dietary, pharmaceutical, and cosmetic uses, there exists a need for a low-cost and efficient method of producing biological oils containing these fatty acids.

BRIEF SUMMARY OF THE INVENTION

The present invention is directed to an isolated microorganism of the species selected from the group consisting of *Pseudozyma aphidis, Pseudozyma rugulosa, Sporidiobolus pararoseus,* and *Rhodotorula ingeniosa,* wherein the microorganism is capable of producing a microbial oil comprising less than 30% by weight saturated fatty acids.

In some embodiments, the isolated microorganisms are capable of producing fatty acids in an amount that is at least 30% by weight of the dry cell weight. In some embodiments, the isolated microorganisms are capable of producing fatty acids in an amount that is at least 40%, at least 50%, or at least 60% by weight of the dry cell weight.

In some embodiments, the isolated microorganisms of the invention are capable of producing a microbial oil comprising greater than 30% by weight, greater than 40% by weight, greater than 50% by weight, or greater than 60% by weight oleic acid.

In some embodiments, the isolated microorganisms of the invention are capable of producing a microbial oil comprising greater than 5% by weight, greater than 10% by weight, or greater than 15% by weight linoleic acid.

In some embodiments, the isolated microorganisms of the invention are capable of producing a microbial oil comprising less than 25% by weight saturated fatty acids. In some embodiments, the microorganisms of the invention are capable of producing a microbial oil comprising less than 25% by weight, less than 20% by weight, or less than 15% by weight palmitic acid.

In some embodiments, the isolated microorganisms of the invention are capable of producing a microbial oil comprising less than 10% by weight, or less than 5% by weight long chain polyunsaturated fatty acids of 20 or more carbon chain length.

The present invention is directed to an isolated microorganism of the species selected from the group consisting of *Pseudozyma aphidis, Pseudozyma rugulosa,* and *Rhodotorula ingeniosa,* wherein the microorganism is capable of producing fatty acids in an amount that is at least 30% by weight of the dry cell weight. In some embodiments, the isolated microorganisms of the species selected from the group consisting of *Pseudozyma aphidis, Pseudozyma rugulosa,* and *Rhodotorula ingeniosa* are capable of producing fatty acids in an amount that is at least 40% or at least 50% by weight of the dry cell weight.

The present invention is further directed to an isolated microorganism of the *Sporidiobolus pararoseus* species, wherein the microorganism is capable of producing fatty acids in an amount that is at least 50% by weight of the dry cell weight. In some embodiments, the isolated microorganisms of the *Sporidiobolus pararoseus* species are capable of producing fatty acids in an amount that is at least 55% or at least 60% by weight of the dry cell weight.

The present invention is directed to an isolated microorganism of the species selected from the group consisting of *Pseudozyma aphidis*, *Pseudozyma rugulosa*, *Sporidiobolus pararoseus*, and *Rhodotorula ingeniosa*, wherein the microorganism is capable of producing a microbial oil comprising 0.5% to 30% by weight saturated fatty acids, and wherein the microorganism is capable of producing fatty acids in an amount that is 30% to 80% by weight of the dry cell weight.

The present invention is also directed to an isolated microorganism of the species selected from the group consisting of *Pseudozyma aphidis*, *Pseudozyma rugulosa*, *Sporidiobolus pararoseus*, and *Rhodotorula ingeniosa*, wherein the microorganism is capable of producing a microbial oil comprising 30% to 70% by weight oleic acid and 5% to 30% by weight linoleic acid.

The present invention is further directed to an isolated microorganism of the *Sporidiobolus pararoseus* species, wherein the microorganism is capable of producing fatty acids in an amount that is 50% to 80% by weight of the dry cell weight, and wherein the microorganism is capable of producing a microbial oil comprising 5% to 30% by weight linoleic acid.

The present invention is directed to an isolated microorganism deposited under ATCC Accession No. PTA-11615, an isolated microorganism deposited under ATCC Accession No. PTA-11616, and an isolated microorganism deposited under ATCC Accession No. PTA-11617.

The present invention is also directed to an isolated microorganism having the characteristics of the microorganism deposited under ATCC Accession No. PTA-11615, an isolated microorganism having the characteristics of the microorganism deposited under ATCC Accession No. PTA-11616, and an isolated microorganism having the characteristics of the microorganism deposited under ATCC Accession No. PTA-11617.

The present invention is directed to an isolated biomass comprising an isolated microorganism of the invention or mixtures of the isolated microorganisms of the invention.

In some embodiments, at least 30% by weight of the dry cell weight of the isolated biomass are fatty acids.

The present invention is also directed to a culture comprising an isolated microorganism of invention or mixtures of the isolated microorganisms of the invention.

In some embodiments, the culture comprises at least 5 g/L of biomass of the isolated microorganism.

The present invention is directed to a method for producing a microbial oil, comprising: growing an isolated microorganism of the invention or mixtures of isolated microorganisms of the invention in a culture to produce a microbial oil.

In some embodiments, the method further comprises extracting the microbial oil.

In some embodiments, the isolated microorganisms are grown in the presence of a carbon source selected from the group consisting of sucrose, glucose, fructose, xylose, glycerol, mannose, arabinose, lactose, galactose, maltose, cellulose, lignocellulose, and combinations thereof.

In some embodiments, the method produces a culture comprising biomass of the isolated microorganism, and the culture comprises at least 5 g/L of the biomass.

The present invention is further directed to microbial oils produced by the methods of the invention, and to the use of the isolated microorganism, biomass, culture, or microbial oil of the invention for the manufacture of a food, supplement, cosmetic, or pharmaceutical composition for a non-human animal or human.

BRIEF DESCRIPTION OF THE DRAWINGS/FIGURES

FIG. 1 shows the DNA sequences of strain 28428 (ATCC Accession No. PTA-11615) (SEQ ID NOs: 1 and 2).

FIG. 2 shows the phylogenetic tree of strain 28428 (ATCC Accession No. PTA-11615) D1/D2 DNA sequences.

FIG. 3 shows the phylogenetic tree of strain 28428 (ATCC Accession No. PTA-11615) ITS DNA sequences.

FIG. 4 shows the DNA sequences of strain 29404 (ATCC Accession No. PTA-11616) (SEQ ID NOs: 3 and 4).

FIG. 5 shows the phylogenetic tree of strain 29404 (ATCC Accession No. PTA-11616) D1/D2 DNA sequences.

FIG. 6 shows the phylogenetic tree of strain 29404 (ATCC Accession No. PTA-11616) ITS DNA sequences.

FIG. 7 shows the DNA sequences of strain 29794 (ATCC Accession No. PTA-11617) (SEQ ID NOs:5 and 6).

FIG. 8 shows the phylogenetic tree of strain 29794 (ATCC Accession No. PTA-11617) D1/D2 DNA sequences.

FIG. 9 shows the phylogenetic tree of strain 29794 (ATCC Accession No. PTA-11617) ITS DNA sequences.

DETAILED DESCRIPTION OF THE INVENTION

The present invention is directed to isolated microorganism of the *Pseudozyma aphidis*, *Pseudozyma rugulosa*, *Sporidiobolus pararoseus*, or *Rhodotorula ingeniosa* species, as well as microorganisms having the characteristics of the isolated microorganisms, and biomasses, microbial oils, compositions, and cultures thereof. The present invention is also directed to methods of producing microbial oils from the isolated microorganisms of the invention, and methods of using the isolated microorganisms, biomasses, cultures, and microbial oils. The isolated microorganisms described herein are highly productive as compared to prior isolates and produce unique fatty acid profiles, characterized in part by high levels of short-chain unsaturated fatty acids, low levels of saturated fatty acids, and low levels of long chain polyunsaturated fatty acids.

In some embodiments, the isolated microorganisms of the invention are capable of producing fatty acids in an amount that is at least 30% by weight of the dry cell weight. In some embodiments, the isolated microorganisms of the invention are capable of producing fatty acids in an amount that is at least 35%, at least 40%, at least 45%, at least 50%, at least 55%, at least 60%, or at least 65% by weight of the dry cell weight. In some embodiments, the isolated microorganisms of the invention are capable of producing fatty acids in an mount that is 30% to 80% by weight of the dry cell weight, 35% to 80% by weight of the dry cell weight, 40% to 80% by weight of the dry cell weight, 45% to 75% by weight of the dry cell weight, 50% to 75% by weight of the dry cell weight, 55% to 70% by weight of the dry cell weight, or 60% to 70% by weight of the dry cell weight.

In some embodiments, the invention is directed to an isolated microorganism of the *Pseudozyma aphidis*, *Pseudozyma rugulosa*, or *Rhodotorula ingeniosa* species, wherein the microorganism is capable of producing fatty acids in an amount that is at least 30% by weight of the dry cell weight. In some embodiments, an isolated microorganisms of the *Pseudozyma aphidis*, *Pseudozyma rugulosa*, or *Rhodotorula ingeniosa* species are capable of producing fatty acids in an amount that is at least 35%, at least 40%, at least 45%, at least 50%, or at least 55% by weight of the dry cell weight. In some embodiments, the isolated microorganisms of the *Pseudozyma aphidis, Pseudozyma rugulosa*, or *Rhodotorula ingeniosa* species are capable of producing fatty acids in an amount that is 30% to 80% by weight of the dry cell weight, 35% to 75% by weight of the dry cell weight, 40% to 70% by weight of the dry cell weight, 45% to 70% by weight of the dry cell weight, 50% to 65% by weight of the dry cell weight, or 55% to 65% by weight of the dry cell weight.

The present invention is also directed to an isolated microorganism of the *Sporidiobolus pararoseus* species, wherein the microorganism is capable of producing fatty acids in an amount that is greater than 45% by weight of the dry cell weight. In some embodiments, the isolated microorganisms of the *Sporidiobolus pararoseus* species are capable of producing fatty acids in an amount that is at least 46%, at least 47%, at least 48%, at least 49%, at least 50%, at least 55%, at least 60%, at least 65%, or at least 70% by weight of the dry cell weight. In some embodiments, the isolated microorganisms of the *Sporidiobolus pararoseus* species are capable of producing fatty acids in an amount that is 30% to 85% by weight of the dry cell weight, 40% to 80% by weight of the dry cell weight, 45% to 80% by weight of the dry cell weight, 46% to 80% by weight of the dry cell weight, 47% to 80% by weight of the dry cell weight, 48% to 80% by weight of the dry cell weight, 49% to 80% by weight of the dry cell weight, 50% to 80% by weight of the dry cell weight, 55% to 75% by weight of the dry cell weight, 60% to 70% by weight of the dry cell weight, or 65% to 70% by weight of the dry cell weight.

In some embodiments, the invention is directed to an isolated microorganism of the *Pseudozyma aphidis, Pseudozyma rugulosa, Sporidiobolus pararoseus*, or *Rhodotorula ingeniosa* species, wherein the microorganism is capable of producing a microbial oil comprising greater than 30% by weight oleic acid (18:1n-9). In some embodiments, the isolated microorganism of the invention is capable of producing a microbial oil comprising greater than 35%, greater than 40%, greater than 45%, greater than 50%, greater than 55%, greater than 60%, or greater than 65% by weight of oleic acid. In some embodiments, the isolated microorganism of the invention is capable of producing a microbial oil comprising from 30% to 70% by weight of oleic acid, from 35% to 70% by weight of oleic acid, from 40% to 65% by weight of oleic acid, from 45% to 65% by weight of oleic acid, from 50% to 65% by weight of oleic acid, from 55% to 65% by weight of oleic acid, or from 60% to 65% by weight of oleic acid.

In some embodiments, the isolated microorganism of the invention is capable of producing a microbial oil comprising greater than 5% by weight linoleic acid (18:2). In some embodiments, the isolated microorganism of the invention is capable of producing a microbial oil comprising greater than 7%, greater than 10%, greater than 12%, greater than 1.5%, greater than 17%, or greater than 20% by weight of linoleic acid. In some embodiments, the isolated microorganism of the invention is capable of producing a microbial oil comprising from 5% to 30% by weight of linoleic acid, from 7% to 28% by weight of linoleic acid, from 10% to 25% by weight of linoleic acid, from 12% to 25% by weight of linoleic acid, from 15% to 25% by weight of linoleic acid, from 17% to 25% by weight of linoleic acid, or from 20% to 23% by weight of linoleic acid.

In some embodiments, the isolated microorganism of the invention is capable of producing a microbial oil comprising less than 30% by weight saturated fatty acids. In some embodiments, the isolated microorganism of the invention is capable of producing a microbial oil comprising less than 25%, less than 20%, less than 15%, less than 10%, less than 8%, or less than 5% by weight of saturated fatty acids. In some embodiments, the isolated microorganism of the invention is capable of producing a microbial oil comprising from 0.5% to 30% by weight of saturated fatty acids, from 1% to 25% by weight of saturated fatty acids, horn 1% to 20% by weight of saturated fatty acids, from 1% to 15% by weight of saturated fatty acids, from 1% to 10% by weight of saturated fatty acids, from 1% to 8% by weight of saturated fatty acids, or from 1% to 5% by weight of saturated fatty acids.

In some embodiments, the isolated microorganism of the invention is capable of producing a microbial oil comprising less than 25% by weight palmitic acid (16:0). In some embodiments, the isolated microorganism of the invention is capable of producing a microbial oil comprising less than 23%, less than 20%, less than 18%, or less than 15% by weight of palmitic acid. In some embodiments, the isolated microorganism of the invention is capable of producing a microbial oil comprising from 0.5% to 25% by weight of palmitic acid, from 1% to 20% by weight of palmitic acid, from 1% to 18% by weight of palmitic acid, from 1% to 15% by weight of palmitic acid, from 5% to 15% by weight of palmitic acid, or from 10% to 15% by weight of palmitic acid.

In some embodiments, the isolated microorganism of the invention is capable of producing a microbial oil comprising less than 10% by weight long chain polyunsaturated fatty acids (LC-PUFAs) of 20 or more carbon chain length. In some embodiments, the isolated microorganism of the invention is capable of producing a microbial oil comprising less than 8%, less than 5%, less than 4%, less than 3%, less than 2%, less than 1%, or less than 0.5% by weight of LCPUFAs of 20 or more carbon chain length. In some embodiments, the isolated microorganism of the invention is capable of producing microbial oil comprising from 0% to 10% by weight, from 0% to 8% by weight, from 0% to 5% by weight, from 0% to 4% by weight, from 0% to 3% by weight, from 0% to 2% by weight, or from 0% to 1% by weight of LCPUFAs of 20 or more carbon chain length. In some embodiments, the isolated microorganism of the invention is capable of producing a microbial oil with no detectable amount of LCPUFAs of 20 or more carbon chain length.

In some embodiments, the isolated microorganism of the invention is capable of producing a microbial oil comprising less than 10%, less than 8%, less than 5%, less than 4%, less than 3%, less than 2%, less than 1%, or less than 0.5% by weight of docosahexaenoic acid (DHA). In some embodiments, the isolated microorganism of the invention is capable of producing a microbial oil comprising from 0% to 10% by weight of DHA, from 0% to 8% by weight of DHA, from 0% to 5% by weight of DHA, from 0% to 4% by weight of DHA, from 0% to 3% by weight of DHA, from 0% to 2% by weight of DHA, or from 0% to 1% by weight of DHA. In some embodiments, the isolated microorganism of the invention is capable of producing a microbial oil with no detectable amount of DHA.

In some embodiments, the isolated microorganism of the invention is capable of producing a microbial oil comprising less than 1.0%, less than 8%, less than 5%, less than 4%, less than 3%, less than 2%, less than 1%, or less than 0.5% by weight of eicosapentaenoic acid (EPA). In some embodiments, the isolated microorganism of the invention is capable of producing a microbial oil comprising from 0% to 10% by weight of EPA, from 0% to 8% by weight of EPA, from 0% to 5% by weight of EPA, from 0% to 4% by weight of EPA, from 0% to 3% by weight of EPA, from 0% to 2% by weight of EPA, or from 0% to 1% by weight of EPA. In some embodiments, the isolated microorganism of the invention is capable of producing a microbial oil with no detectable amount of EPA.

In some embodiments, the isolated microorganism of the invention is capable of producing a microbial oil comprising less than 10%, less than 8%, than 5%, less than 4%, less than 3%, less than 2%, less than 1%, or less than 0.5% by weight of omega-3 docosapentaenoic acid (DPA n-3). In some embodiments, the isolated microorganism of the invention is capable of producing a microbial oil comprising from 0% to 10% by weight of DPA n-3, from 0% to 8% by weight of DPA n-3, from 0% to 5% by weight of DPA n-3, from 0% to 4% by weight of DPA n-3, from 0% to 3% by weight of DPA n-3, from 0% to 2% by weight of DPA n-3, or from 0% to 1% by weight of DPA n-3. In some embodiments, the isolated microorganism of the invention is capable of producing a microbial oil with no detectable amount of DPA n-3.

In some embodiments, the isolated microorganism of the invention is capable of producing a microbial oil comprising less than 10%, less than 8%, less than 5%, less than 4%, less than 3%, less than 2%, less than 1%, or less than 0.5% by weight of omega-6 docosapentaenoic acid (DPA n-6). In some embodiments, the isolated microorganism of the invention is capable of producing a microbial oil comprising from 0% to 10% by weight of DPA n-6, from 0% to 8% by weight of DPA n-6, from 0% to 5% by weight of DPA n-6, from 0% to 4% by weight of DPA n-6, from 0% to 3% by weight of DPA n-6, from 0% to 2% by weight of DPA n-6, or from 0% to 1% by weight of DPA n-6. In some embodiments, the isolated microorganism of the invention is capable of producing a microbial oil with no detectable amount of DPA n-6.

In some embodiments, the isolated microorganism of the invention is capable of producing a microbial oil comprising less than 10%, less than 8%, less than 5%, less than 4%, less than 3%, less than 2%, less than 1%, or less than 0.5% by weight of omega-6 arachidonic acid (ARA). In some embodiments, the isolated microorganism of the invention is capable of producing a microbial oil comprising from 0% to 10% by weight of ARA, from 0% to 8% by weight of ARA, from 0% to 5% by weight of ARA, from 0% to 4% by weight of ARA, from 0% to 3% by weight of ARA, from 0% to 2% by weight of ARA, or from 0% to 1% by weight of ARA. In some embodiments, the isolated microorganism of the invention is capable of producing a microbial oil with no detectable amount of ARA.

In some embodiments, the invention is directed to an isolated microorganism of the *Pseudozyma aphidis, Pseudozyma rugulosa, Sporidiobolus pararoseus*, or *Rhodotorula ingeniosa* species, wherein the microorganism is capable of producing a microbial oil comprising 0.5% to 30% by weight saturated fatty acids, and wherein the microorganism is capable of producing fatty acids in an amount that is 30% to 80% by weight of the dry cell weight. In some embodiments, the isolated microorganism of the *Pseudozyma aphidis, Pseudozyma rugulosa, Sporidiobolus pararoseus*, or *Rhodotorula ingeniosa* species is capable of producing a microbial oil comprising 1% to 25% by weight saturated fatty acids, and is capable of producing fatty acids in an amount that is 40% to 80% by weight of the dry cell weight. In some embodiments, the isolated microorganism of the *Pseudozyma aphidis, Pseudozyma rugulosa, Sporidiobolus pararoseus*, or *Rhodotorula ingeniosa* species is capable of producing a microbial oil comprising 1% to 20% by weight saturated fatty acids, and is capable of producing fatty acids in an amount that is 50% to 80% by weight of the dry cell weight. In some embodiments, the isolated microorganism of the *Pseudozyma aphidis, Pseudozyma rugulosa, Sporidiobolus pararoseus*, or *Rhodotorula ingeniosa* species is capable of producing a microbial oil comprising 1% to 20% by weight saturated fatty acids, and is capable of producing fatty acids in an amount that is 55% to 75% by weight of the dry cell weight. In some embodiments, the isolated microorganism of the *Pseudozyma aphidis, Pseudozyma rugulosa, Sporidiobolus pararoseus*, or *Rhodotorula ingeniosa* species is capable of producing a microbial oil comprising 1% to 20% by weight saturated fatty acids, and is capable of producing fatty acids in an amount that is 60% to 75% by weight of the dry cell weight. In some embodiments, the isolated microorganism of the *Pseudozyma aphidis, Pseudozyma rugulosa, Sporidiobolus pararoseus*, or *Rhodotorula ingeniosa* species is capable of producing a microbial oil comprising 1% to 20% by weight saturated fatty acids, and is capable of producing fatty acids in an amount that is 60% to 70% by weight of the dry cell weight.

In some embodiments, the invention is directed to an isolated microorganism of the *Pseudozyma aphidis, Pseudozyma rugulosa, Sporidiobolus pararoseus*, or *Rhodotorula ingeniosa* species, wherein the microorganism is capable of producing a microbial oil comprising 30% to 70% by weight oleic acid and 5% to 30% by weight linoleic acid. In some embodiments, the isolated microorganism of the *Pseudozyma aphidis, Pseudozyma rugulosa, Sporidiobolus pararoseus*, or *Rhodotorula ingeniosa* species is capable of producing a microbial oil comprising 35% to 70% by weight oleic acid and 5% to 25% by weight linoleic acid. In some embodiments, the isolated microorganism of the *Pseudozyma aphidis, Pseudozyma rugulosa, Sporidiobolus pararoseus*, or *Rhodotorula ingeniosa* species is capable of producing a microbial oil comprising 40% to 65% by weight oleic acid and 5% to 20% by weight linoleic acid. In some embodiments, the isolated microorganism of the *Pseudozyma aphidis, Pseudozyma rugulosa, Sporidiobolus pararoseus*, or *Rhodotorula ingeniosa* species is capable of producing a microbial oil comprising 45% to 65% by weight oleic acid and 5% to 20% by weight linoleic acid. In some embodiments, the isolated microorganism of the *Pseudozyma aphidis, Pseudozyma rugulosa, Sporidiobolus pararoseus*, or *Rhodotorula ingeniosa* species is capable of producing a microbial oil comprising 50% to 65% by weight oleic acid and 7% to 20% by weight linoleic acid. In some embodiments, the isolated microorganism of the *Pseudozyma aphidis, Pseudozyma rugulosa, Sporidiobolus pararoseus*, or *Rhodotorula ingeniosa* species is capable of producing a microbial oil comprising 55% to 65% by weight oleic acid and 7% to 15% by weight linoleic acid.

In some embodiments, the invention is directed to an isolated microorganism of the *Sporidiobolus pararoseus* species, wherein the microorganism is capable of producing fatty acids in an amount that is 50% to 80% by weight of the dry cell weight, and wherein the microorganism is capable of producing a microbial oil comprising 5% to 30% by weight linoleic acid. In some embodiments, the isolated microorganism of the *Sporidiobolus pararoseus* species is capable of producing fatty acids in an amount that is 55% to 75% by weight of the dry cell weight, and wherein the microorganism is capable of producing a microbial oil comprising 5% to 25% by weight linoleic acid. In some embodiments, the isolated microorganism of the *Sporidiobolus pararoseus* species is capable of producing fatty acids in an amount that is 60% to 70% by weight of the dry cell weight, and wherein the microorganism is capable of producing a microbial oil comprising 7% to 20% by weight linoleic acid. In some embodiments, the isolated microorganism of the *Sporidiobolus pararoseus* species is capable of producing fatty acids in an amount that is 65% to 70% by weight of the dry cell weight, and wherein the microorganism is capable of producing a microbial oil comprising 7% to 15% by weight linoleic acid.

In some embodiments, the invention is directed to an isolated microorganism of the species deposited under ATCC Accession No. PTA-11615. The isolated microorganism is also known herein as Pseudozyma aphidis/rugulosa ATCC PTA-11615. The isolated microorganism associated with ATCC Accession No. PTA-11615 was deposited under the Budapest Treaty on Jan. 26, 2011 at the American Type Culture Collection, Patent Depository, 10801 University Boulevard, Manassas, Va. 20110-2209.

In some embodiments, the invention is directed to an isolated microorganism of the species deposited under ATCC Accession No. PTA-11616. The isolated microorganism is also known herein as *Sporidiobolus pararoseus* ATCC PTA-11616. The isolated microorganism associated with ATCC Accession No. PTA-11616 was deposited under the Budapest Treaty on Jan. 26, 2011 at the American Type Culture Collection, Patent Depository, 10801 University Boulevard, Manassas, Va. 20110-2209.

In some embodiments, the invention is directed to an isolated microorganism of the species deposited under ATCC Accession No. PTA-11617. The isolated microorganism is also known herein as *Rhodotorula ingeniosa* ATCC PTA-11617. The isolated microorganism associated with ATCC Accession No. PTA-11617 was deposited under the Budapest Treaty on Jan. 26, 2011 at the American Type Culture Collection, Patent Depository, 10801 University Boulevard, Manassas, Va. 20110-2209.

In some embodiments, the invention is directed to an isolated microorganism having the characteristics of the microorganism deposited under ATCC Accession No. PTA-11615, ATCC Accession No. PTA-11616, or ATCC Accession No. PTA-11617. The characteristics of the species deposited under ATCC Accession No. PTA-11615, ATCC Accession No. PTA-11616, or ATCC Accession No. PTA-11617 include its growth and phenotypic properties (examples of phenotypic properties include morphological and reproductive properties), its physical and chemical properties (such as dry weights and lipid profiles), and its gene sequences. In some embodiments, the isolated microorganisms of the invention have substantially identical phenotypic properties of the microorganism deposited under ATCC Accession No. PTA-11615, ATCC Accession No. PTA-11616, or ATCC Accession No. PTA-11617. In some embodiments, the isolated microorganisms of the invention have substantially identical growth properties of the microorganisms deposited under ATCC Accession No. PTA-11615, ATCC Accession No. PTA-11616, or ATCC Accession No. PTA-11617.

The invention is further directed to an isolated biomass comprising the isolated microorganisms of the invention. An isolated biomass of the invention is a harvested cellular biomass obtained by any conventional method for the isolation of a microbial biomass.

The biomass of the invention contains a high level of fatty acids. In some embodiments, at least 30% by weight of the dry cell weight of the biomass of the invention are fatty acids. In some embodiments, at least 40%, at least 45%, at least 50%, at least 55%, at least 60%, or at least 65% by weight of the dry cell weight of the biomass of the invention are fatty acids. In some embodiments, the biomass of the invention comprises from 30% to 75%, from 40% to 75%, from 45% to 70%, from 50% to 70%, from 55% to 65% fatty acids by the dry cell weight of the biomass.

The invention is further directed to a culture comprising one or more isolated microorganisms of the invention. Various fermentation parameters for inoculating, growing, and recovering yeast strains are known in the art. Any conventional medium for growth of yeasts can be used.

The cultures of the invention contain a high amount of biomass per liter of culture broth, indicating efficient growth of the isolated microorganisms. In some embodiments, the cultures comprise at least 1 g/L of biomass of the isolated microorganisms of the invention. In some embodiments, the cultures comprise at least 2 g/L, at least 3 g/L, at least 4 g/L, at least 5 g/L, at least 6 g/L, at least 7 g/L, at least 8 g/L, at least 9 g/L, or at least 10 g/L of biomass of the isolated microorganisms of the invention. In some embodiments, the cultures comprises 1 g/L to 10 g/L, 2 g/L to 10 g/L, 3 g/L to 10 g/L, 4 g/L to 10 g/L, 5 g/L to 10 g/L, 6 g/L to 10 g/L, 7 g/L to 10 g/L, 8 g/L to 10 g/L, or 9 g/L to 10 g/L of biomass of the isolated microorganisms of the invention.

The present invention is further directed to methods of producing microbial oils.

In some embodiments, the method comprises growing an isolated microorganism of the invention or mixtures thereof in a culture to produce a microbial oil. The isolated microorganisms of the invention can be grown in the presence of various carbon sources, including, for example, sucrose, glucose, fructose, xylose, glycerol, mannose, arabinose, lactose, galactose, maltose, cellulose, lignocellulose, or combinations thereof. The method can further comprise extracting the microbial oil. The oil can be extracted from a freshly harvested biomass or can be extracted from a previously harvested biomass that has been stored under conditions that prevent spoilage, Known methods can be used to culture a microorganism of the invention, to isolate a biomass from the culture, to extract a microbial oil from the biomass, and to analyze the fatty acid profile of oils extracted from the biomass.

The invention is further directed to a microbial oil produced by the methods of the invention. In some embodiments, the microbial oil comprises a fatty acid profile having the same characteristics as the fatty acid profile of the isolated microorganisms of the invention. A microbial oil of the invention can be any oil derived from a microorganism, including, for example: a crude oil extracted from the biomass of the microorganism without further processing; a refined oil that is obtained by treating a crude microbial oil with further processing steps such as refining, bleaching, and/or deodorizing; a diluted microbial oil obtained by diluting a crude or refined microbial oil; or an enriched oil that is obtained, for example, by treating a crude or refined microbial oil with further methods of purification to increase the concentration of a fatty acid in the oil.

The invention is also directed to the use of the isolated microorganism, biomass, culture, or microbial oil of the invention far the manufacture of a food, dietary supplement, cosmetic, or pharmaceutical composition for a non-human animal or human.

Compositions

The invention is further directed to compositions comprising an isolated microorganism of the invention, an isolated biomass of the invention, a microbial oil of the invention, or combinations thereof.

An isolated microorganism, biomass, or microbial oil of the invention can be further chemically or physically modified or processed based on the requirements of the composition by any known technique.

Microorganism cells or biomasses can be dried prior to use in a composition by methods including, but not limited to, freeze drying, air drying, spray drying, tunnel drying, vacuum drying (lyophilization), or a similar process. Alternatively, a harvested and washed biomass can be used directly in a composition without drying.

Microbial oils of the invention can be used as starting material to more efficiently produce a product enriched in a fatty acid. For example, the microbial oils of the invention can be subjected to various purification techniques known in the art, such as distillation or urea adduction, to produce a higher potency product with higher concentrations of a particular fatty acid. The microbial oils of the invention can also be used in chemical reactions to produce compounds derived from fatty acids in the oils, such as esters and salts of a fatty acid.

A composition of the invention can include one or more excipients. As used herein, "excipient" refers to a component, or mixture of components, that is used in a composition of the present invention to give desirable characteristics to the composition, including foods as well as pharmaceutical, cosmetic, and industrial compositions. An excipient of the present invention can be described as a "pharmaceutically acceptable" excipient when added to a pharmaceutical composition, meaning that the excipient is a compound, material, composition, salt, and/or dosage form which is, within the scope of sound medical judgment, suitable for contact with the tissues of human beings and animals without excessive toxicity, irritation, allergic response, or other problematic complications over the desired duration of contact commensurate with a reasonable benefit/risk ratio. In some embodiments, the term "pharmaceutically acceptable" means approved by a regulatory agency of the Federal or a state government or listed in the U.S. Pharmacopeia or other generally recognized international pharmacopeia for use in animals, and more particularly in humans. Various excipients can be used. In some embodiments, the excipient can be, but is not limited to, an alkaline agent, a stabilizer, an antioxidant, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, Remington: The Science and Practice of Pharmacy, 21$^{st}$ ed. (2005). Inclusion of an excipient in a particular classification herein (e.g., "solvent") is intended to illustrate rather than limit the role of the excipient. A particular excipient can fall within multiple classifications.

Compositions of the invention include, but are not limited to, food products, pharmaceutical compositions, cosmetics, and industrial compositions.

In some embodiments, the composition is a food product. A food product is any food for animal or human consumption, and includes both solid and liquid compositions. A food product can be an additive to animal or human foods. Foods include, but are not limited to common foods; liquid products, including milks, beverages, therapeutic drinks, and nutritional drinks; functional foods; supplements; nutraceuticals; infant formulas, including formulas for pre-mature infants; foods for pregnant or nursing women; foods for adults; geriatric foods; and animal foods.

In some embodiments, an isolated microorganism, biomass, or microbial oil of the invention can be used directly as or included as an additive within one or more of: an oil, shortening, spread, other fatty ingredient, beverage; sauce, dairy-based or soy-based food (such as milk, yogurt, cheese and ice-cream), a baked good, a nutritional product, e.g., as a nutritional supplement (in capsule or tablet form), a vitamin supplement, a diet supplement, a powdered drink, a finished or semi-finished powdered food product, and combinations thereof.

A partial list of food compositions that can include a microbial oil of the invention includes, but is not limited to, soya based products (milks, ice creams, yogurts, drinks, creams, spreads, whiteners); soups and soup mixes; doughs, batters, and baked food items including, for example, fine bakery wares, breakfast cereals, cakes, cheesecakes, pies, cupcakes, cookies, bars, breads, rolls, biscuits, muffins, pastries, scones, croutons, crackers, sweet goods, snack cakes, pies, granola/snack bars, and toaster pastries; candy; hard confectionery; chocolate and other confectionery; chewing gum; liquid food products, for example milks, energy drinks, infant formula, carbonated drinks, teas, liquid meals, fruit juices, fruit-based drinks, vegetable-based drinks; multivitamin syrups, meal replacers, medicinal foods, and syrups; powdered beverage mixes; pasta; processed fish products; processed meat products; processed poultry products; gravies and sauces; condiments (ketchup, mayonnaise, etc.); vegetable oil-based spreads; dairy products; yogurt; butters; frozen dairy products; ice creams; frozen desserts; frozen yogurts; semi-solid food products such as baby food; puddings and gelatin desserts; processed and unprocessed cheese; pancake mixes; food bars including energy bars; waffle mixes; salad dressings; replacement egg mixes; nut and nut-based spreads; salted snacks such as potato chips and other chips or crisps, corn chips, tortilla chips, extruded snacks, popcorn, pretzels, potato crisps, and nuts; specialty snacks such as dips, dried fruit snacks, meat snacks, pork rinds, health food bars and rice/corn cakes.

In some embodiments, a microbial oil of the invention can be used to supplement infant formula. Infant formula can be supplemented with a microbial oil of the invention alone or in combination with a physically refined oil derived from an arachidonic acid (ARA)-producing microorganism.

In some embodiments, the composition is an animal feed. An "animal" means any non-human organism belonging to the kingdom Animalia, and includes, without limitation, aquatic animals and terrestrial animals. The term "animal feed" or "animal food" refers to any food intended for non-human animals, whether for fish; commercial fish; ornamental fish; fish larvae; bivalves; mollusks; crustaceans; shellfish; shrimp; larval shrimp; artemia; rotifers; brine shrimp; filter feeders; amphibians; reptiles; mammals; domestic animals; farm animals; zoo animals; sport animals; breeding stock; racing animals; show animals; heirloom animals; rare or endangered animals; companion animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; rodents such as mice, rats, hamsters and guinea pigs; and so on. An animal feed includes, but is not limited to, an aquaculture feed, a domestic animal feed including pet feed, a zoological animal feed, a work animal feed, a livestock feed, or a combination thereof.

In some embodiments, the composition is a feed or feed supplement for any animal whose meat or products are consumed by humans, such as any animal from which meat, eggs, or milk is derived for human consumption. When fed to such animals, nutrients such as certain fatty acids can be incorporated into the flesh, milk, eggs or other products of such animals to increase their content of these nutrients.

In some embodiments, the composition is a spray-dried material that can be crumbled to form particles of an appropriate size for consumption by zooplankton, artemia, rotifers, and filter feeders. In some embodiments, the zooplankton, artemia, or rotifers fed by the composition are in turn fed to fish larvae, fish, shellfish, bivalves, or crustaceans.

In some embodiments, the composition is a pharmaceutical composition. Suitable pharmaceutical compositions include, but are not limited to, an anti-inflammatory composition, a drug for treatment of coronary heart disease, a drug for treatment of arteriosclerosis, a chemotherapeutic agent, an active excipient, an osteoporosis drug, an anti-depressant, an anti-convulsant, an anti *Helicobacter pylori* drug, a drug for treatment of neurodegenerative disease, a drug for treatment of degenerative liver disease, an antibiotic, a cholesterol lowering composition, and a triglyceride lowering composition. In some embodiments, the composition is a medical food. A medical food includes a food that is in a composition to be consumed or administered externally under the supervision of a physician and that is intended for the specific dietary management of a condition, for which distinctive nutritional requirements, based on recognized scientific principles, are established by medical evaluation.

in some embodiments, the microbial oil can be formulated in a dosage form. Dosage forms can include, but are not limited to, tablets, capsules, cachets, pellets, pills, powders and granules, and parenteral dosage forms, which include, but are not limited to, solutions, suspensions, emulsions, and dry powders comprising an effective amount of the microbial oil. It is also known in the art that such formulations can also contain pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. Administration forms can include, but are not limited to, tablets, dragees, capsules, caplets, and pills, which contain the microbial oil and one or more suitable pharmaceutically acceptable carriers.

For oral administration, the microbial oil can be combined with pharmaceutically acceptable carriers well known in the art. Such carriers enable the microbial oils of the invention to be formulated as tablets, pills, dragees, capsules, liquids, gels, syrups, slurries, suspensions and the like, for oral ingestion by a subject to be treated. In some embodiments, the dosage form is a tablet, pill or caplet. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl cellulose, sodium carboxymethyl cellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate, Pharmaceutical preparations that can be used orally include, but are not limited to, push-fit capsules made of gelatin, as well as soft, sealed capsules made of gelatin and a plasticizer, such as glycerol or sorbitol.

In some embodiments, the composition is a cosmetic. Cosmetics include, but are not limited to, emulsions, creams, lotions, masks, soaps, shampoos, washes, facial creams, conditioners, make-ups, bath agents, and dispersion liquids. Cosmetic agents can be medicinal or non-medicinal.

In some embodiments, the composition is an industrial composition. In some embodiments, the composition is a starting material for one or more manufactures. A manufacture includes, but is not limited to, a polymer; a photographic photosensitive material; a detergent; an industrial oil; or an industrial detergent. For example, U.S. Pat. No. 7,259,006 describes use of DHA-containing fat and oil for production of behenic acid and production of photographic sensitive materials using behenic acid.

In some embodiments, the composition is a lipid-based biofuel manufactured by converting the biological oil of the invention into lipid-based biofuel through known means in the art, such as through transesterifying the biological oil to produce biodiesel, Different uses of the biological oils of the present invention for lipid-based biofuel purposes include, but are not limited to, uses as heating oil, transportation biodiesel, jet fuel, fuel additives, specialty fuels and lubricants. In some embodiments, the conversion of biological oils into lipid-based biofuels involves chemical processes and refining techniques known in the art which may also produce or be used to produce specialty chemical compounds similar to petroleum, distillates.

Kits Comprising the Compositions

The invention is further directed to kits or packages containing one or more units of a composition of the invention. Kits or packages can include units of a food product, pharmaceutical composition, cosmetic, or industrial composition comprising the isolated microorganism, biomass, or microbial oil of the invention, or combinations thereof. Kits or packages can also include an additive comprising the isolated microorganism, biomass, or microbial oil of the invention, or combinations thereof for preparation of a food, cosmetic, pharmaceutical composition, or industrial composition.

In some embodiments, the kit or package contains one or more units of a pharmaceutical composition to be administered according to the methods of the present invention. The kit or package can contain one dosage unit, or more than one dosage unit (i.e., multiple dosage units). If multiple dosage units are present in the kit or package, the multiple dosage units can be optionally arranged for sequential administration.

The kits of the present invention can optionally contain instructions associated with the units or dosage forms of the kits. Such instructions can be in a form prescribed by a governmental agency regulating the manufacture, use or sale of pharmaceutical products, which notice reflects approval by the agency of the manufacture, use or sale for human administration to treat a condition or disorder. The instructions can be in any form which conveys information on the use of the units or dosage forms in the kit according to the methods of the invention. For example, the instructions can be in the form of printed matter, or in the form of a pre-recorded media device.

In the course of examination of a patient, a medical professional can determine that administration of one of the methods of the present invention is appropriate for the patient, or the physician can determine that the patient's condition can be improved by the administration of one of the methods of the present invention. Prior to prescribing any regimen, the physician can counsel the patient, for example, on the various risks and benefits associated with the regimen. The patient can be provided full disclosure of all known and suspected risks associated with the regimen. Such counseling can be provided verbally, as well as in written form. In some embodiments, the physician can provide the patient with literature materials on the regimen, such as product information, educational materials, and the like.

The present invention is also directed to methods of educating consumers about the methods of treatment, the method comprising distributing the dosage forms with consumer information at a point of sale. In some embodiments, the distribution will occur at a point of sale having a pharmacist or healthcare provider.

The term "consumer information" can include, but is not limited to, an English language text, non-English language text, visual image, chart, telephone recording, website, and access to a live customer service representative. In some embodiments, consumer information will provide directions for use of the dosage forms according to the methods of the present invention, appropriate age use, indication, contraindications, appropriate dosing, warnings, telephone number of website address. In some embodiments, the method further comprises providing professional information to relevant persons in a position to answer consumer questions regarding use of the disclosed regimens according to the methods of the present invention. The term "professional information" includes, but is not limited to, information concerning the regimen when administered according to the methods of the present invention that is designed to enable a medical professional to answer customer questions.

A "medical professional," includes, for example, a physician, physician assistant, nurse practitioner, pharmacist and customer service representative.

EXAMPLES

Example 1

Identifications were determined for three yeast strains: ATCC Accession No. PTA-11615 (Strain 28428), ATCC Accession No. PTA-11616 (Strain 29404) and ATCC Accession. No, PTA-11617 (Strain 29794). The yeasts were plated on Malt Agar, DNA extractions were conducted and ribosomal gene sequence analysis performed. Sequence homology comparisons were done between the D1D2 and ITS regions and known DNA sequences from yeast strains in the public databases. Morphological examination was also conducted for comparisons to known yeast species.

Strain 28428 DNA sequences (FIG. 1) matched 100% with the Genbank sequence for the Type strain of *Pseudozyma aphidis* in the first region analyzed (D1/D2 domains of the Large subunit) and differed by 1 mismatch from the Type strain of *Pseudozyma rugulosa* (FIG. 2). In the second region (ITS) out of 545 possible matches, the strain showed 2 mismatches from the Type strain of *P. aphidis* and again 1 from the Type strain of *P. rugulosa* (FIG. 3). The two species appear to be closely related showing genetic variability within and between them. Morphological characteristics are also very similar between *P. aphidis* and *P. rugulosa* and matched the morphology observations in strain 28428, which showed flat, dull, yellowish-cream colonies with fringed margin and fusiform cells, variable in size, with polar budding on short denticles. Based on the data in hand, it is not possible to distinguish the identification more specifically than as either *P. aphidis* or *P. rugulosa*.

Strain 29404 DNA sequences (FIG. 4) matched perfectly in both regions with the Genbank sequences for *Sporidiobolus pararoseus* CBS 484, Comparison to the Type strain of the species CBS 491 had 2 mismatches in D1D2 and 2 in ITS (FIGS. 5 & 6). Morphological characteristics (ovoid cells, single or in short chains, and shiny coral red colonies with a smooth surface and an entire margin) confirmed the identification. The identification of this strain is *Sporidiobolus pararoseus*.

Strain 29794 DNA sequences (FIG. 7) showed an identical sequence match to the type strain of *Rhodotorula ingeniosa* (CBS 4240) in the D1D2 domains (FIG. 8) and only one mismatch out of 590 possible matches in the ITS regions (FIG. 9), which is possibly due to intra-specific variability. Cell and colony morphology (ovoid to cylindrical cells, single or in pairs, a thin capsule and yellowish, glistening, highly mucoid colonies) confirmed the identification. The identification of this strain is *R. ingeniosa*.

Example 2

Isolated microorganisms of *Sporidiobolus pararoseus* and *Rhodotorula ingeniosa* were grown in ¼X BFGM medium (Table 1). Each strain was picked from an agar plate, and inoculated into a shake flask. The shake flask was then used to inoculate another flask (250 ml Erlenmeyer flask containing 50 ml of medium) that was then grown for 7 days. After 7 days the flask was harvested by centrifugation, the pellet was washed with water and centrifuged again. The final pellet was freeze dried, the weight was measured and then total fat (total fatty acids) and fatty acid profile were determined by FAME procedure.

The isolated microorganism of *Pseudozyma aphidis/rugulosa* was grown in the media below (Media 2) and the fatty acid profile was determined. Results of the fatty acid profile analysis fir all three strains are shown in Table 2.

Media 2:
15 g/L Reef Crystal Artificial Sea salts
1 g/L glucose
1 g/L monosodium glutamate
0.2 g/L yeast extract
1 mL/L vitamin mix*
mL/L PII trace metal mix**
0.1 g/L penicillin G
0.1 g/L streptomycin sulfate
*vitamin mix contains 100 mg/L thiamine, 0.5 mg/L biotin, 0.5 g/L cyanocobalmin
**PII trace metal mix contains:
6.0 g/L $Na_2EDTA$
0.29 g/L $FeCl_3.6H_2O$
6.84 g/L $H_3BO_3$
0.86 g/L $MnCl_2.4H_2O$
0.06 g/L $ZnCl_2$
0.026 g/L $CoCl_2.6H_2O$
0.052 g/L $NiSO_4.6H_2O$
0.002 g/L $CuSO_4.5H_2O$
0.005 g/L $Na_2MoO_4.2H_2O$

TABLE 1

¼ × BFGM Medium

| Component | Amount per liter (g) | [Stock] (g/l) | mL of stock to use per liter | Na | K | Mg | Ca | Cl | Fe | Cu | Mn | Co | Zn |
|---|---|---|---|---|---|---|---|---|---|---|---|---|---|
| | | | | | | g/l | | | | | mg/l | | |
| NaCl | 0.625 | dry | | 0.25 | | | | 0.38 | | | | | |
| KCl | 1 | 50 | 20 ml | | 0.52 | | | 0.48 | | | | | |
| MgSO4•7H2O | 5 | 227 | 22 ml | | | 0.47 | | | | | | | |
| (NH4)2SO4 | 0.05 | 190 | 0.2625 ml | | | | | | | | | | |

TABLE 1-continued

¼ × BFGM Medium

| Component | Amount per liter (g) | [Stock] (g/l) | mL of stock to use per liter | | Na | K | Mg | Ca | Cl | Fe | Cu | Mn | Co | Zn |
|---|---|---|---|---|---|---|---|---|---|---|---|---|---|---|
| | | | | | g/l | | | | | mg/l | | | | |
| CaCl2 2H2O | 0.29 | dry | | | | | | 0.08 | 0.14 | | | | | |
| MSG monohydrate | 0.5 | dry | | | | | | | | | | | | |
| Tastone 154 | 0.5 | dry | | | | | | | | | | | | |
| HEPES (100 mM) pH 7 | 23.8 | dry | | | | | | | | | | | | |
| KH2PO4 | 0.025 | 56.5 | 0.4425 ml add after autoclaving | | | | | | | | | | | |
| Sucrose | 50 | 500 | 100 ml add after autoclaving | | | | | | | | | | | |
| Trace Metals | | see below | 2 ml add after autoclaving | | | | | | | | | | | |
| Vitamins | | see below | 1 ml add after autoclaving | | | | | | | | | | | |
| Trace Metal Solution | | | | | | | | | | | | | | |
| Citric Acid | 1.0 g | dry | | | | | | | | | | | | |
| FeSO4•7H2O | 10.3 mg | 5.15 | | | | | | | | 2.07 | | | | |
| MnCl2•4H2O | 3.1 mg | 1.55 | | | | | | | | | | 0.86 | | |
| ZnSO4•7H2O | 1.93 mg | 0.965 | | | | | | | | | | | | 0.44 |
| CoCl2•6H2O | 0.04 mg | 0.02 | | | | | | | | | | | 0.01 | |
| Na2MoO4•2H2O | 0.04 mg | 0.02 | | | | | | | | | | | | |
| CuSO4•5H2O | 2.07 mg | 1.035 | | | | | | | | | 0.53 | | | |
| NiSO4•6H2O | 2.07 mg | 1.035 | | | | | | | | | | | | |
| pH to 2.5 with HCl | | | | | | | | | | | | | | |
| Vitamin Solution | | | | | | | | | | | | | | |
| Vitamin B12 | 0.16 mg | 0.16 | | | | | | | | | | | | |
| Thiamine | 9.75 mg | 9.75 | | | | | | | | | | | | |
| CaPantothenate | 3.33 mg | 3.33 | | | | | | | | | | | | |

Ion Totals (ppm) 995.8536

TABLE 2

| | Media | | | |
|---|---|---|---|---|
| | ¼ BFGM | | | Media 2 |
| Microorganism | | | | |
| | Rhodotorula ingeniosa | | Sporidiobolus pararoseus | Pseudozyma aphidis/rugulosa |
| Sugar | | | | |
| | Sucrose | Xylose | Sucrose | Glucose |
| Temperature (° C.) | 27 | 27 | 22.5 | 30° C. |
| Biomass g/L | 9.506 | 5.338 | 8.79 | |
| pH | 6.9 | 6.78 | 6.68 | |
| % 08:0 | 0.00 | 0.00 | 0.00 | |
| % 09:0 | 0.00 | 0.00 | 0.00 | |
| % 10:0 | 0.00 | 0.00 | 0.00 | |
| % 11:0 | 0.00 | 0.00 | 0.00 | |
| % 11:1 | 0.00 | 0.00 | 0.00 | |
| % 12:0 | 0.00 | 0.00 | 0.00 | |
| % 12:1 | 0.00 | 0.00 | 0.00 | |
| % 13:0 | 0.17 | 0.18 | 0.00 | |
| % 13:1 | 0.00 | 0.00 | 0.00 | |
| % 14:0 | 0.58 | 0.73 | 0.00 | 0.8 |
| % 14:1 | 0.00 | 0.00 | 0.00 | Trace (<1.0%) |
| % 15:1 | 0.00 | 0.00 | 0.00 | |
| % 16:0 | 18.14 | 19.62 | 16.02 | 21.9 |
| % 16:1 | 0.64 | 0.69 | 0.29 | 6.6 |
| % 16:2 | 0.00 | 0.00 | 0.00 | |
| % 16:3 | 0.00 | 0.00 | 0.00 | |
| % 17:0 | 0.00 | 0.00 | 0.11 | |
| % 18:0 | 3.88 | 4.13 | 4.86 | 2.1 |
| % 18:1 n-9 | 61.79 | 59.54 | 60.78 | 40.4 |
| % 18:1 n-7 | 0.43 | 0.19 | 0.00 | |
| % 18:2 | 8.83 | 9.76 | 9.75 | 24.7 |
| % 18:3 n-6 | 0.06 | 0.00 | 0.00 | |
| % 18:3 n-3 | 2.71 | 2.54 | 4.72 | |
| % 18:4 n-3 | 0.00 | 0.00 | 0.00 | |
| % 20:0 | 1.18 | 0.92 | 0.00 | 0.8 |
| % 20:1 n-9 | 0.29 | 0.30 | 0.00 | 0.5 |
| % 20:2 | 0.00 | 0.00 | 0.00 | |
| % 20:3 n-9 | 0.00 | 0.00 | 0.00 | |
| % 20:3 n-6 | 0.00 | 0.00 | 0.00 | |
| % 20:3 n-3 | 0.00 | 0.00 | 0.00 | |
| % 20:4 ARA | 0.00 | 0.14 | 0.00 | |
| % 20:5 n-3 EPA | 0.00 | 0.00 | 0.00 | |
| % 22:0 | 0.54 | 0.55 | 0.00 | 1.1 |
| % 22:1 | 0.00 | 0.00 | 0.00 | |
| % 22:2 | 0.17 | 0.21 | 0.00 | |
| % 22:3 | 0.00 | 0.00 | 0.00 | |
| % 22:4 n-6 | 0.00 | 0.00 | 0.00 | |
| % 22:5 n-6 | 0.00 | 0.00 | 0.00 | |
| % 22:5 n-3 | 0.00 | 0.00 | 0.00 | |
| % 22:6 n-3 DHA | 0.00 | 0.00 | 0.00 | |
| % 24:0 | 0.21 | 0.20 | 0.00 | 1.1 |
| % 24:1 | 0.00 | 0.00 | 0.00 | |
| % Fat | 55.19 | 45.79 | 65.17 | |
| % Unknown | 0.38 | 0.31 | 3.46 | |

TABLE 2-continued

| | Media | | | |
|---|---|---|---|---|
| | ¼ BFGM | | Media 2 | |
| | Microorganism | | | |
| | *Rhodotorula ingeniosa* | *Sporidiobolus pararoseus* | *Pseudozyma aphidis/rugulosa* | |
| | | Sugar | | |
| | Sucrose | Xylose | Sucrose | Glucose |
| 08:0 | 0.00 | 0.00 | 0 | |
| 09:0 | 0.00 | 0.00 | 0 | |
| 10:0 | 0.00 | 0.00 | 0 | |
| 11:0 | 0.00 | 0.00 | 0 | |
| 11:1 | 0.00 | 0.00 | | |
| 12:0 | 0.00 | 0.00 | 0 | |
| 12:1 | | | 0 | |
| 13:0 | 6.04 | 5.70 | 0 | |
| 13:1 | 0.00 | 0.00 | 0 | |
| 14:0 | 20.92 | 22.93 | 0 | |
| 14:1 | 0.00 | 0.00 | 0 | |
| 15:0 INT STD | 681.22 | 684.35 | 112753 | |
| 15:1 | 0.00 | 0.00 | 0 | |
| 16:0 | 654.11 | 617.77 | 110650 | |
| 16:1 | 23.02 | 21.84 | 2025 | |
| 16:2 | | | | |
| 16:3 | | | | |
| 17:0 | 0.00 | 0.00 | 759 | |
| 18:0 | 140.00 | 129.99 | 33583 | |
| 18:1 n-9 | 2227.57 | 1874.95 | 419870 | |
| 18:1 n-7 | 15.60 | 6.08 | 0 | |
| 18:2 | 318.37 | 307.24 | 67375 | |
| 18:3 n-6 | 2.23 | 0.00 | 0 | |
| 18:3 n-3 | 97.78 | 79.91 | 32596 | |
| 18:4 n-3 | | | | |
| 20:0 | 42.43 | 28.86 | 0 | |
| 20:1 n-9 | 10.38 | 9.59 | 0 | |
| 20:2 | 0.00 | 0.00 | 0 | |
| 20:3 n-9 | | | | |
| 20:3 n-6 | 0.00 | 0.00 | 0 | |
| 20:3 n-3 | 0.00 | 0.00 | 0 | |
| 20:4 ARA | 0.00 | 4.40 | 0 | |
| 20:5 n-3 EPA | 0.00 | 0.00 | 0 | |
| 22:0 | 19.48 | 17.18 | 0 | |
| 22:1 | 0.00 | 0.00 | 0 | |
| 22:2 | 6.08 | 6.67 | 0 | |
| 22:3 | 0.00 | 0.00 | 0 | |
| 22:4 n-6 | 0.00 | 0.00 | 0 | |
| 22:5 n-6 | 0.00 | 0.00 | 0 | |
| 22:5 n-3 | 0.00 | 0.00 | 0 | |
| 22:6 n-3 DHA | 0.00 | 0.00 | 0 | |
| 23:0 INT STD | 0.00 | 0.00 | 0 | |
| 24:0 | 7.55 | 6.45 | 0 | |
| 24:1 | 0.00 | 0.00 | 0 | |
| Total Area | 4286.43 | 3833.56 | 803514 | |
| Total | 3605.22 | 3149.22 | 690761 | |

Example 3

Isolated microorganisms having matching DNA sequences to that of ATCC Accession No, PTA-11615 (*Pseudozyma aphidis/rugulosa*; Strain 28428), ATCC Accession No. PTA-11616 (*Sporidiobolus pararoseus*; Strain 29404) and ATCC Accession No. PTA-11617 (*Rhodotorula ingeniosa*; Strain 29794) were grown and the total fat (total fatty acids) and fatty acid profiles were determined. Results are shown in Tables 3 and 4.

TABLE 3

| | ID | | | | | | | | |
|---|---|---|---|---|---|---|---|---|---|
| | *Rhodotorula ingeniosa* | | *Sporidiobolus pararoseus* | | | | | | |
| | | | Strain # | | | | | | |
| | 29764 | 29764 | 29664 | 29405 | 29412 | 29459 | 29556 | 29568 | 29573 |
| Dry Weight (g/l) | 4.23 | 11.054 | 6.44 | 9.89 | 6.23 | 6.86 | 4.85 | 1.3 | 8.46 |
| Medium | ¼ BFGM | ¼ BFGM | ¼ BFGM | ¼ BFGM | ¼ BFGM | ¼ BFGM | ¼ BFGM | ¼ BFGM | ¼ BFGM |
| Sugar | Xylose | Sucrose | sucrose | sucrose | sucrose | sucrose | sucrose | sucrose | sucrose |
| 8:0 | 0.00 | 0.00 | 0.00 | 0.00 | 0.00 | 0.00 | 0.00 | 0.00 | 0.00 |
| 9:0 | 0.00 | 0.00 | 0.00 | 0.00 | 0.00 | 0.00 | 0.00 | 0.00 | 0.00 |
| 10:0 | 0.00 | 0.00 | 0.00 | 0.00 | 0.00 | 0.00 | 0.00 | 0.00 | 0.00 |
| 11:0 | 0.00 | 0.00 | 0.00 | 0.00 | 0.00 | 0.00 | 0.00 | 0.00 | 0.00 |
| 11:1 | 0.00 | 0.00 | 0.00 | 0.00 | 0.00 | 0.00 | 0.00 | 0.00 | 0.00 |
| 12:0 | 0.00 | 0.07 | 0.00 | 0.00 | 0.00 | 0.00 | 0.03 | 0.00 | 0.00 |
| 12:1 | 0.00 | 0.00 | 0.00 | 0.00 | 0.00 | 0.00 | 0.00 | 0.00 | 0.00 |
| 13:0 | 0.22 | 0.15 | 0.09 | 0.12 | 0.13 | 0.09 | 0.13 | 0.18 | 0.15 |
| 13:1 | 0.00 | 0.00 | 0.00 | 0.00 | 0.00 | 0.00 | 0.00 | 0.00 | 0.00 |
| 14:0 | 0.81 | 0.71 | 0.00 | 0.61 | 0.85 | 0.65 | 0.86 | 0.80 | 0.88 |
| 14:1 | 0.00 | 0.00 | 0.00 | 0.00 | 0.00 | 0.00 | 0.00 | 0.00 | 0.00 |
| 15:1 | 0.00 | 0.00 | 0.03 | 0.00 | 0.00 | 0.00 | 0.00 | 0.11 | 0.00 |
| 16:0 | 21.71 | 22.03 | 16.96 | 16.52 | 18.79 | 16.01 | 19.53 | 23.82 | 19.22 |
| 16:1 | 0.57 | 0.66 | 0.44 | 0.32 | 0.20 | 0.21 | 0.34 | 0.50 | 0.41 |
| 16:2 | 0.00 | 0.00 | 0.00 | 0.00 | 0.00 | 0.00 | 0.00 | 0.00 | 0.00 |
| 16:3 | 0.00 | 0.00 | 0.00 | 0.00 | 0.00 | 0.00 | 0.00 | 0.00 | 0.00 |
| 17:0 | 0.00 | 0.00 | 0.17 | 0.19 | 0.09 | 0.17 | 0.13 | 0.18 | 0.14 |
| 18:0 | 6.58 | 6.27 | 4.04 | 4.67 | 7.70 | 5.83 | 5.72 | 10.66 | 4.30 |
| 18:1n9 | 52.63 | 53.65 | 60.31 | 59.97 | 0.00 | 62.94 | 56.56 | 40.16 | 59.19 |
| 18:1n7 | 0.28 | 0.59 | 0.00 | 0.00 | 61.36 | 0.00 | 0.00 | 0.00 | 0.00 |

TABLE 3-continued

| | | | | | | | | | |
|---|---|---|---|---|---|---|---|---|---|
| 18:2 | 10.99 | 10.52 | 11.53 | 9.96 | 5.84 | 8.84 | 11.03 | 16.40 | 9.89 |
| 18:3n6 | 0.08 | 0.08 | 0.00 | 0.00 | 0.00 | 0.00 | 0.00 | 0.00 | 0.00 |
| 18:3n3 | 3.73 | 2.76 | 2.15 | 5.24 | 1.97 | 1.59 | 2.78 | 4.19 | 2.86 |
| 18:4n3 | 0.00 | 0.00 | 0.00 | 0.00 | 0.00 | 0.00 | 0.00 | 0.00 | 0.00 |
| 20:0 | 0.84 | 1.14 | 0.79 | 0.68 | 0.83 | 0.78 | 0.87 | 0.38 | 0.68 |
| 20:1n9 | 0.26 | 0.23 | 0.31 | 0.06 | 0.29 | 0.35 | 0.22 | 0.08 | 0.09 |
| 20:2 | 0.00 | 0.00 | 0.05 | 0.00 | 0.00 | 0.00 | 0.00 | 0.00 | 0.00 |
| 20:3n9 | 0.00 | 0.00 | 0.00 | 0.00 | 0.00 | 0.00 | 0.00 | 0.00 | 0.00 |
| 20:3n6 | 0.00 | 0.00 | 0.12 | 0.11 | 0.00 | 0.13 | 0.10 | 0.14 | 0.11 |
| 20:3n3 | 0.00 | 0.00 | 0.00 | 0.00 | 0.00 | 0.00 | 0.00 | 0.00 | 0.00 |
| 20:4n6 ARA | 0.20 | 0.11 | 0.00 | 0.00 | 0.00 | 0.00 | 0.00 | 0.00 | 0.00 |
| 20:5n3 EPA | 0.00 | 0.00 | 0.00 | 0.00 | 0.00 | 0.00 | 0.00 | 0.00 | 0.00 |
| 22:0 | 0.64 | 0.50 | 1.14 | 0.64 | 0.94 | 1.27 | 0.88 | 0.69 | 0.91 |
| 22:1 | 0.00 | 0.00 | 0.00 | 0.00 | 0.00 | 0.00 | 0.00 | 0.00 | 0.00 |
| 22:2 | 0.18 | 0.13 | 0.00 | 0.00 | 0.00 | 0.00 | 0.00 | 0.00 | 0.00 |
| 22:3 | 0.00 | 0.00 | 0.00 | 0.00 | 0.00 | 0.00 | 0.00 | 0.00 | 0.00 |
| 22:4n6 | 0.00 | 0.00 | 0.00 | 0.00 | 0.00 | 0.00 | 0.00 | 0.00 | 0.00 |
| 22:5n6 | 0.00 | 0.00 | 0.00 | 0.00 | 0.00 | 0.00 | 0.00 | 0.00 | 0.00 |
| 22:5n3 | 0.00 | 0.00 | 0.00 | 0.00 | 0.00 | 0.00 | 0.00 | 0.00 | 0.00 |
| 22:6n3 | 0.00 | 0.00 | 0.00 | 0.00 | 0.00 | 0.00 | 0.00 | 0.00 | 0.00 |
| 24:0 | 0.29 | 0.19 | 0.00 | 0.43 | 0.49 | 0.84 | 0.41 | 1.72 | 0.58 |
| 24:1 | 0.00 | 0.00 | 0.00 | 0.00 | 0.00 | 0.00 | 0.00 | 0.00 | 0.00 |
| Fat | 39.04 | 52.86 | 67.01 | 56.02 | 59.60 | 63.32 | 64.44 | 40.38 | 64.00 |
| Unknown | 0.00 | 0.23 | 1.88 | 0.48 | 0.51 | 0.30 | 0.43 | 0.00 | 0.58 |

| | ID *Sporidiobolus pararoseus* Strain # | | | | | | | | |
|---|---|---|---|---|---|---|---|---|---|
| | 29577 | 29588 | 29591 | 29594 | 29631 | 29655 | 29596 | 29631 | 29655 |
| Dry Weight (g/l) | 3.87 | 5.46 | 6.31 | 7.3 | 4.73 | 9.41 | 8.12 | 4.73 | 9.41 |
| Medium | ¼ BFGM | ¼ BFGM | ¼ BFGM | ¼ BFGM | ¼ BFGM | ¼ BFGM | ¼ BFGM | ¼ BFGM | ¼ BFGM |
| Sugar | sucrose | sucrose | sucrose | sucrose | sucrose | sucrose | sucrose | sucrose | sucrose |
| 8:0 | 0.00 | 0.00 | 0.00 | 0.00 | 0.00 | 0.00 | 0.00 | 0.00 | 0.00 |
| 9:0 | 0.00 | 0.00 | 0.00 | 0.00 | 0.00 | 0.00 | 0.00 | 0.00 | 0.00 |
| 10:0 | 0.00 | 0.00 | 0.00 | 0.00 | 0.00 | 0.00 | 0.00 | 0.00 | 0.00 |
| 11:0 | 0.00 | 0.00 | 0.00 | 0.00 | 0.00 | 0.00 | 0.00 | 0.00 | 0.00 |
| 11:1 | 0.00 | 0.00 | 0.00 | 0.00 | 0.00 | 0.00 | 0.00 | 0.00 | 0.00 |
| 12:0 | 0.00 | 0.00 | 0.00 | 0.00 | 0.00 | 0.00 | 0.00 | 0.00 | 0.00 |
| 12:1 | 0.00 | 0.00 | 0.00 | 0.00 | 0.00 | 0.00 | 0.00 | 0.00 | 0.00 |
| 13:0 | 0.27 | 0.18 | 0.16 | 0.14 | 0.21 | 0.15 | 0.38 | 0.21 | 0.15 |
| 13:1 | 0.00 | 0.00 | 0.00 | 0.00 | 0.00 | 0.00 | 0.00 | 0.00 | 0.00 |
| 14:0 | 0.55 | 0.63 | 0.57 | 0.94 | 0.53 | 0.86 | 0.57 | 0.53 | 0.86 |
| 14:1 | 0.00 | 0.00 | 0.00 | 0.00 | 0.00 | 0.00 | 0.00 | 0.00 | 0.00 |
| 15:1 | 0.14 | 0.07 | 0.00 | 0.04 | 0.12 | 0.00 | 0.11 | 0.12 | 0.00 |
| 16:0 | 20.04 | 18.50 | 16.84 | 19.22 | 18.33 | 19.98 | 17.98 | 18.33 | 19.98 |
| 16:1 | 0.33 | 0.41 | 0.34 | 0.60 | 0.48 | 0.41 | 0.31 | 0.48 | 0.41 |
| 16:2 | 0.00 | 0.00 | 0.00 | 0.00 | 0.00 | 0.00 | 0.00 | 0.00 | 0.00 |
| 16:3 | 0.00 | 0.00 | 0.00 | 0.00 | 0.00 | 0.00 | 0.00 | 0.00 | 0.00 |
| 17:0 | 0.33 | 0.21 | 0.22 | 0.16 | 0.20 | 0.16 | 0.26 | 0.20 | 0.16 |
| 18:0 | 5.14 | 3.67 | 4.42 | 3.34 | 2.37 | 5.06 | 5.48 | 2.37 | 5.06 |
| 18:1n9 | 42.35 | 57.13 | 57.60 | 60.19 | 56.53 | 54.71 | 46.89 | 56.53 | 54.71 |
| 18:1n7 | 0.00 | 0.00 | 0.00 | 0.00 | 0.00 | 0.00 | 0.00 | 0.00 | 0.00 |
| 18:2 | 25.32 | 14.17 | 14.55 | 10.72 | 15.84 | 13.05 | 21.79 | 15.84 | 13.05 |
| 18:3n6 | 0.00 | 0.00 | 0.00 | 0.00 | 0.00 | 0.00 | 0.00 | 0.00 | 0.00 |
| 18:3n3 | 2.67 | 1.59 | 2.87 | 1.55 | 2.03 | 3.52 | 3.02 | 2.03 | 3.52 |
| 18:4n3 | 0.00 | 0.00 | 0.00 | 0.00 | 0.00 | 0.00 | 0.00 | 0.00 | 0.00 |
| 20:0 | 0.42 | 0.55 | 0.36 | 0.57 | 0.56 | 0.72 | 0.72 | 0.56 | 0.72 |
| 20:1n9 | 0.16 | 0.09 | 0.09 | 0.08 | 0.27 | 0.18 | 0.18 | 0.27 | 0.18 |
| 20:2 | 0.00 | 0.00 | 0.00 | 0.00 | 0.00 | 0.00 | 0.00 | 0.00 | 0.00 |
| 20:3n9 | 0.00 | 0.00 | 0.00 | 0.00 | 0.00 | 0.00 | 0.00 | 0.00 | 0.00 |
| 20:3n6 | 0.21 | 0.17 | 0.13 | 0.12 | 0.20 | 0.00 | 0.00 | 0.20 | 0.00 |
| 20:3n3 | 0.00 | 0.00 | 0.00 | 0.00 | 0.00 | 0.00 | 0.00 | 0.00 | 0.00 |
| 20:4n6 ARA | 0.00 | 0.00 | 0.00 | 0.00 | 0.00 | 0.00 | 0.00 | 0.00 | 0.00 |
| 20:5n3 EPA | 0.00 | 0.00 | 0.00 | 0.00 | 0.00 | 0.00 | 0.00 | 0.00 | 0.00 |
| 22:0 | 0.63 | 0.96 | 0.52 | 0.88 | 0.90 | 0.73 | 0.78 | 0.90 | 0.73 |
| 22:1 | 0.00 | 0.00 | 0.00 | 0.00 | 0.00 | 0.00 | 0.00 | 0.00 | 0.00 |
| 22:2 | 0.00 | 0.00 | 0.00 | 0.00 | 0.00 | 0.00 | 0.00 | 0.00 | 0.00 |
| 22:3 | 0.00 | 0.00 | 0.00 | 0.00 | 0.00 | 0.00 | 0.00 | 0.00 | 0.00 |
| 22:4n6 | 0.00 | 0.00 | 0.00 | 0.00 | 0.00 | 0.00 | 0.00 | 0.00 | 0.00 |
| 22:5n6 | 0.00 | 0.00 | 0.00 | 0.00 | 0.00 | 0.00 | 0.00 | 0.00 | 0.00 |
| 22:5n3 | 0.00 | 0.00 | 0.00 | 0.00 | 0.00 | 0.00 | 0.00 | 0.00 | 0.00 |
| 22:6n3 | 0.00 | 0.00 | 0.00 | 0.00 | 0.00 | 0.00 | 0.00 | 0.00 | 0.00 |
| 24:0 | 1.02 | 0.76 | 0.52 | 0.76 | 0.68 | 0.34 | 0.85 | 0.68 | 0.34 |
| 24:1 | 0.00 | 0.00 | 0.00 | 0.00 | 0.00 | 0.00 | 0.00 | 0.00 | 0.00 |
| Fat | 29.39 | 43.32 | 52.30 | 62.44 | 33.57 | 53.57 | 26.03 | 33.57 | 53.57 |
| Unknown | 0.41 | 0.92 | 0.79 | 0.69 | 0.75 | 0.14 | 0.67 | 0.75 | 0.14 |

TABLE 4

Pseudozyma aphidis/rugulosa

| Strain #: | Strain 28426 |
| --- | --- |
| Media: | Media 2 |
| Sugar: | Glucose |

| Fatty acid | % total fatty acids (area %) |
| --- | --- |
| 14:0 | |
| 14:1 | |
| 16:0 | 27.4 |
| 16:1 | 1.4 |
| 18:0 | 9.6 |
| 18.1 | 31.5 |

TABLE 4-continued

| | |
| --- | --- |
| 18:2 | 28.0 |
| 20:0 | 0.4 |
| 20:1 | 1.6 |
| 22:0 | 0.2 |
| 24:0 | |

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A biofuel comprising a transesterified biological oil, said biological oil comprising less than 30% by weight saturated fatty acids, said biological oil being obtainable from a microorganism of the species selected from the group consisting of *Pseudozyma aphidis*, *Pseudozyma rugulosa*, *Sporidiobolus pararoseus*, and *Rhodotorula ingeniosa*, wherein the microorganism is capable of producing microbial oil comprising less than 30% by weight saturated fatty acids.

2. The biofuel of claim 1, wherein the microorganism is capable of producing fatty acids in an amount that is at least 30% by weight of the dry cell weight.

3. The biofuel of claim 1, wherein the microorganism is capable of producing fatty acids in an amount that is at least 40% by weight of the dry cell weight.

4. The biofuel of claim 1, wherein the microorganism is capable of producing fatty acids in an amount that is at least 50% by weight of the dry cell weight.

5. The biofuel of claim 1, wherein the microorganism is capable of producing fatty acids in an amount that is at least 60% by weight of the dry cell weight.

6. The biofuel of claim 1, wherein the biological oil comprises greater than 30% by weight oleic acid.

7. The biofuel of claim 1, wherein the biological oil comprises greater than 40% by weight oleic acid.

8. The biofuel of claim 1, wherein the biological oil comprises greater than 50% by weight oleic acid.

9. The biofuel of claim 1, wherein the biological oil comprises greater than 60% by weight oleic acid.

10. The biofuel of claim 1, wherein the biological oil comprises greater than 5% by weight linoleic acid.

11. The biofuel of claim 1, wherein the biological oil comprises greater than 10% by weight linoleic acid.

12. The biofuel of claim 1, wherein the biological oil comprises greater than 15% by weight linoleic acid.

13. The biofuel of claim 1, wherein the microorganism is capable of producing a microbial oil comprising less than 25% by weight saturated fatty acids.

14. The biofuel of claim 1, wherein the biological oil comprises less than 25% by weight palmitic acid.

15. The biofuel of claim 1, wherein the biological oil comprises less than 20% by weight palmitic acid.

16. The biofuel of claim 1, wherein the biological oil comprises less than 15% by weight palmitic acid.

17. The biofuel of claim 1, wherein the biological oil comprises less than 10% by weight long chain polyunsaturated fatty acids of 20 or more carbon chain length.

18. The biofuel of claim 1, wherein the biological oil comprises less than 5% by weight long chain polyunsaturated fatty acids of 20 or more carbon chain length.

19. A biofuel comprising a transesterified biological oil, said biological being obtainable from a microorganism of the species selected from the group consisting of *Pseudozyma aphidis*, *Pseudozyma rugulosa*, *Sporidiobolus pararoseus*, and *Rhodotorula ingeniosa*, wherein the microorganism is capable of producing fatty acids in an amount that is at least 30% by weight of dry cell weight.

20. The biofuel of claim 19, wherein the microorganism is capable of producing fatty acids in an amount that is at least 40% by weight of the dry cell weight.

21. The biofuel of claim 19, wherein the microorganism is capable of producing fatty acids in an amount that is at least 50% by weight of the dry cell weight.

22. A biofuel comprising a transesterified biological oil, said biological being obtainable from a microorganism of species *Sporidiobolus pararoseus*, wherein the microorganism is capable of producing fatty acids in an amount that is at least 50% by weight of dry cell weight.

23. The biofuel of claim 22, wherein the microorganism is capable of producing fatty acids in an amount that is at least 55% by weight of the dry cell weight.

24. The biofuel of claim 22, wherein the microorganism is capable of producing fatty acids in an amount that is at least 60% by weight of the dry cell weight.

25. A biofuel comprising a transesterified biological oil, said biological oil comprising 0.5% to 30% by weight saturated fatty acids, said biological oil being obtainable from a microorganism of the species selected from the group consisting of *Pseudozyma aphidis, Pseudozyma rugulosa, Sporidiobolus pararoseus*, and *Rhodotorula ingeniosa*, wherein the microorganism is capable of producing the biological oil comprising 0.5% to 30% by weight saturated fatty acids, and wherein the microorganism is capable of producing fatty acids in an amount that is 30% to 80% by weight of the dry cell weight.

26. A biofuel comprising a transesterified biological oil, said biological oil comprising 30% to 70% by weight oleic acid and 5% to 30% by weight linoleic acid, said biological oil being obtainable from a microorganism of the species selected from the group consisting of *Pseudozyma aphidis, Pseudozyma rugulosa, Sporidiobolus pararoseus*, and *Rhodotorula ingeniosa*, wherein the microorganism is capable of producing the biological oil comprising 30% to 70% by weight oleic acid and 5% to 30% by weight linoleic acid.

27. A biofuel comprising a transesterified biological oil, said biological oil comprising 5% to 30% by weight linoleic acid, said biological oil being obtainable from a microorganism of *Sporidiobolus pararoseus* species, wherein the microorganism is capable of producing fatty acids in an amount that is 50% to 80% by weight of the dry cell weight, and wherein the microorganism is capable of producing a microbial oil comprising 5% to 30% by weight linoleic acid.

28. A biofuel comprising a transesterified biological oil, said biological oil being obtainable from the microorganism deposited under ATCC Accession No. PTA-11615.

29. A biofuel comprising a transesterified biological oil, said biological oil being obtainable from the microorganism deposited under ATCC Accession No. PTA-11616.

30. A biofuel comprising a transesterified biological oil, said biological oil being obtainable from the microorganism deposited under ATCC Accession No. PTA-11617.

31. A biofuel comprising a transesterified biological oil, said biological oil being obtainable from a microorganism having all the characteristics of the microorganism deposited under ATCC Accession No. PTA-11615.

32. A biofuel comprising a transesterified biological oil, said biological oil being obtainable from a microorganism having all the characteristics of the microorganism deposited under ATCC Accession No. PTA-11616.

33. A biofuel comprising a transesterified biological oil, said biological oil being obtainable from a microorganism having all the characteristics of the microorganism deposited under ATCC Accession No. PTA-11617.

34. A biodiesel fuel comprising the biofuel of claim 1.
35. A biodiesel fuel comprising the biofuel of claim 19.
36. A biodiesel fuel comprising the biofuel of claim 22.
37. A biodiesel fuel comprising the biofuel of claim 25.
38. A biodiesel fuel comprising the biofuel of claim 26.
39. A biodiesel fuel comprising the biofuel of claim 27.
40. A biodiesel fuel comprising the biofuel of claim 28.
41. A biodiesel fuel comprising the biofuel of claim 29.
42. A biodiesel fuel comprising the biofuel of claim 30.
43. A biodiesel fuel comprising the biofuel of claim 31.
44. A biodiesel fuel comprising the biofuel of claim 32.
45. A biodiesel fuel comprising the biofuel of claim 33.

* * * * *

SEQUENCE LISTING

<160> NUMBER OF SEQ ID NOS: 6

<210> SEQ ID NO 1
<211> LENGTH: 597
<212> TYPE: DNA
<213> ORGANISM: Pseudozyma aphidis
<220> FEATURE:
<223> OTHER INFORMATION: 28428 D1D2 sequence

<400> SEQUENCE: 1

```
gcatatcaat aagcggagga aaagaaacta acaaggattc ccctagtaac ggcgagtgaa      60
gagggaagag cccaagattg aaagctggcg tcttcggcgt ccgcattgta atctcaagaa     120
gtgttttccg cttcggacca agcctaagtc ccttggaaaa gggcatcata gagggtgata     180
atcccgtaca tggcttggag cgcccgaagc tttgtgatac gctttctaag agtcgagttg     240
tttgggaatg cagctcaaaa tgggtggtaa atgccatcta aggctaaata ttggggagag     300
accgatagcg aacaagtaca gtgatggaaa gatgaaaaga actttgaaaa gagagttaaa     360
cagtacgtga aattgccaaa agggaagggt aggaggtcag agatgcggcc tgggattcag     420
ccttgctttt gcttggtgtt tttcccagat tgcaggccaa cgtcggtttt gggcactgga     480
gaagggtagg aggaacgtgg cacctctcgg ggtgtgttat agcctcctac tggatacagc     540
gaccgagacc gaggacagca gcgtactcgc aagagcgggc cttcgggcac ctttacg        597
```

<210> SEQ ID NO 2
<211> LENGTH: 545
<212> TYPE: DNA
<213> ORGANISM: Pseudozyma aphidis
<220> FEATURE:
<223> OTHER INFORMATION: 28428 ITS sequence

<400> SEQUENCE: 2

```
gttgatacca taggatttga acgtagatga aactcgactg gtaatgcggt cgtctaaaat      60
ctaaaaacaa cttttggcaa cggatctctt ggttctccca tcgatgaaga acgcagcgaa     120
ttgcgataag taatgtgaat tgcagaagtg aatcatcgaa tctttgaacg caccttgcgc     180 tccggcaga tctaatctgg ggagcatgcc tgtttgaggg ccgcgaattg tttcgaacga     240
cagctttctt atttagttga gaaagctggc ggatcggtat tgagggtctt gccatcttcc     300
acggtggctc cctcgaaatg cattagcgca tccattcgat aggcaagacg gacgaaagct     360
cgttatttcg cccacgtctt tccctgccgg gttttgataa tatcaggact tcggagagga     420
gaggcgcagg gtcgaggagc tggacgcgac gttttgctgg ttggagtgct tctgaaccc     480
```

```
gcccatgcct cccttcttcg gaaggagagg aagggattta atttcaattc atcggcctca    540
gattg                                                                545

<210> SEQ ID NO 3
<211> LENGTH: 563
<212> TYPE: DNA
<213> ORGANISM: Sporidiobolus pararoseus
<220> FEATURE:
<223> OTHER INFORMATION: 29404 D1D2 sequence

<400> SEQUENCE: 3 attccccctag tagcggcgag cgaagcggga aaagctcaaa tttgtaatct ggcgtcttcg    60
acgtccgagt tgtaatctcg agaagtgttt tccgtgatag accgcataca agtctcttgg    120
aacagagcgt catagtggtg agaacccagt acacgatgcg gatgcctatt actttgtgat    180
acactttcga agagtcgagt tgtttgggaa tgcagctcaa attgggtggt aaattccatc    240
taaagctaaa tattggcgag agaccgatag cgaacaagta ccgtgaggga agatgaaaa    300 gcactttgga aagagagtta acagtacgtg aaattgttgg aagggaaaca catgcagtga    360
tacttgctat tcggggcaac tcgattggca ggcccgcatc agttttttcgg ggcggaaaat    420 cgtagagaga aggtagcagt ttcggctgtg ttatagctct ttactggatt cgccctgggg    480
gactgaggaa cgcagcgtgc ttttagcatg agcttcggct tatccacgct taggatgcgg    540
gtttatggct gtatatgacc cgt                                            563

<210> SEQ ID NO 4
<211> LENGTH: 558
<212> TYPE: DNA
<213> ORGANISM: Sporidiobolus pararoseus
<220> FEATURE:
<223> OTHER INFORMATION: 29404 ITS sequence

<400> SEQUENCE: 4
aacaaggttt ccgtaggtga acctgcggaa ggatcattat tgaaaacaag ggtgtccaat    60
ttaacttgga acccaaactt ctcaattcta actttgtgca tctgtattaa tggcgagcaa    120
cttcggttgt gagccttcac ttacaaaaca ctagtctatg aatgtaaaat ttttataaca    180
aataaaaact ttcaacaacg gatctcttgg ctctcgcatc gatgaagaac gcagcgaaat    240
gcgatacgta atgtgaattg cagaattcag tgaatcatcg aatctttgaa cgcatcttgc    300
gctctctggt attccggaga gcatgtctgt ttgagtgtca tgaattcttc aacccaatct    360
tttcttgtaa tcgattggtg tttggattct gagcgttgct ggcgtttgcc tagctcgttc    420
gtaatacatt agcatcccta atacaagttt ggattgactt ggcgtaatag actattcgct    480
aaggattcgg tggaaacatc gagccaactt cattaaggaa gctcctaatt taaagtcta    540 cctttttgatt agatctca                                                 558

<210> SEQ ID NO 5
<211> LENGTH: 581
<212> TYPE: DNA
<213> ORGANISM: Rhodotorula ingeniosa
<220> FEATURE:
<223> OTHER INFORMATION: 29794 D1D2 sequence

<400> SEQUENCE: 5
taagcggagg aaaagaaact aacaaggatt cccctagtaa cggcgagtga agcgggaaga    60
gctcaaattt gtaatctggc actttcagtg tccgagttgt aatctcgaga agtgttttcc    120
gcgccggacc gcatacaagt ctgttggaat acagcgtcat agtggtgaga accccgtaac    180
```

```
-continued tgatgcggat gcccggtgct ttgtgataca ctttcgaaga gtcgagttgt ttgggaatgc    240
agctcaaatt gggtggtaaa ttccatctaa agctaaatat tggcgagaga ccgatagcga    300
acaagtaccg tgagggaaag atgaaaagca ctttggaaag agagttaaca gtacgtgaaa    360
ttgttggaag ggaaacgctt gaagtcgagac ttgctatttg gagttcagcc catggtgtat    420
tcttcaattt gcaggccagc atcagttttc gagggtggaa aatcgtagtt tgaatgtagc    480
agtttcggct gtgttatagc tttctactgg attcatcttt ggggactgag gaacgcagtg    540
cgcttttagc aaggctctcg agctttacgc acttaggatg c                        581

<210> SEQ ID NO 6
<211> LENGTH: 590
<212> TYPE: DNA
<213> ORGANISM: Rhodotorula ingeniosa
<220> FEATURE:
<223> OTHER INFORMATION: 29794 ITS sequence

<400> SEQUENCE: 6
gacctgcgga aggatcatta gtgaatttag cgcatctgct ttgcagagcg tgacctccac     60
tttctaactc tgtgcactta atggcggaag agatgaaata tgctcttctg cggctcattt    120
tataacacta gttaaagaat gtaacgaaat atcgaaacaa aaaaaaactt tcaacaacgg    180
atctcttggc tctcgcatcg atgaagaacg cagcgaaatg tgataagtaa tgtgaattgc    240
agaattcagt gaatcatcga atctttgaac gcaccttgcg ctccctggta ttccggggag    300
catgtctgtt tgagtgtcat gaactcttca acccaccggt ttcttgtaaa ctggctggtg    360
tttggtttct gagtgttgct cgttcttgtg actgagctca ttcgtaatat atgagcatct    420
ctaattcgaa ttcggattga ctcagtgtaa tagactattc gctgaggaca cacctagtgt    480
ggccgaataa gataattgta gaagcttcta acccttctag tcattttaag attagacctc    540
agatcagata ggactacccg ctgaacttaa gcatatcaat aagcggagga               590
```